US008748376B2

(12) United States Patent
Ludvigsen et al.

(10) Patent No.: US 8,748,376 B2
(45) Date of Patent: Jun. 10, 2014

(54) STABLE FORMULATIONS OF PEPTIDES

(75) Inventors: Svend Ludvigsen, Lynge (DK); Morten Schlein, København (DK); Tine Elisabeth Gottschalk Bøving, Lyngby (DK); Claude Bonde, Lyngby (DK); Anne-Mette Lilleøre, Charlottenlund (DK); Dorthe Kot Engelund, Holte (DK); Bjarne Rønfeldt Nielsen, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 471 days.

(21) Appl. No.: 12/643,330

(22) Filed: Dec. 21, 2009

(65) Prior Publication Data

US 2010/0173844 A1 Jul. 8, 2010

Related U.S. Application Data

(62) Division of application No. 11/667,040, filed as application No. PCT/EP2005/055946 on Nov. 14, 2005, now abandoned.

(60) Provisional application No. 60/635,311, filed on Dec. 10, 2004, provisional application No. 60/682,724, filed on May 19, 2005.

(30) Foreign Application Priority Data

| Nov. 12, 2004 | (DK) | 2004 01753 |
| Dec. 8, 2004 | (DK) | 2004 01906 |
| May 13, 2005 | (EP) | 05104050 |
| May 18, 2005 | (EP) | 05104172 |
| Nov. 11, 2005 | (WO) | PCT/EP2005/055916 |

(51) Int. Cl.
*A61K 38/26* (2006.01)
*C07K 14/605* (2006.01)

(52) U.S. Cl.
USPC ........................................ 514/7.2; 530/308

(58) Field of Classification Search
CPC ......................... C07K 14/605; A61K 38/26
See application file for complete search history.

(56) References Cited

U.S. PATENT DOCUMENTS

| 4,468,346 | A | 8/1984 | Paul et al. |
| 5,206,219 | A | 4/1993 | Desai |
| 5,272,135 | A | 12/1993 | Takruri |
| 5,455,331 | A | 10/1995 | Pearce |
| 5,652,216 | A | 7/1997 | Kornfelt et al. |
| 5,705,483 | A | 1/1998 | Galloway et al. |
| 6,133,229 | A | 10/2000 | Gibson et al. |
| 6,184,201 | B1 | 2/2001 | Drucker et al. |
| 6,245,572 | B1 | 6/2001 | Wall |
| 6,268,343 | B1 | 7/2001 | Knudsen et al. |
| 6,274,553 | B1 | 8/2001 | Furuya et al. |
| 6,284,727 | B1 | 9/2001 | Kim et al. |
| 6,380,357 | B2 | 4/2002 | Hermeling et al. |
| 6,384,016 | B1 | 5/2002 | Kaarsholm |
| 6,444,788 | B1 | 9/2002 | Staby |
| 6,518,241 | B2* | 2/2003 | Matthiesen ................ 514/5.9 |
| 6,586,399 | B1 | 7/2003 | Drucker |
| 6,844,321 | B2 | 1/2005 | Arentsen |
| 7,022,674 | B2 | 4/2006 | DeFelippis et al. |
| 7,049,284 | B2 | 5/2006 | Drucker et al. |
| 7,056,886 | B2 | 6/2006 | Issacs |
| 7,112,567 | B2 | 9/2006 | Bridon et al. |
| 7,238,663 | B2 | 7/2007 | DeFelippis et al. |
| 2001/0014666 | A1 | 8/2001 | Hermeling et al. |
| 2001/0027180 | A1 | 10/2001 | Isaacs |
| 2002/0151467 | A1 | 10/2002 | Leung |
| 2003/0027996 | A1* | 2/2003 | Staby ...................... 530/416 |
| 2003/0060412 | A1 | 3/2003 | Prouty, Jr. et al. |
| 2003/0069182 | A1 | 4/2003 | Rinella, Jr. |
| 2003/0119734 | A1* | 6/2003 | Flink et al. ................. 514/12 |
| 2003/0158101 | A1 | 8/2003 | Drucker |
| 2003/0207802 | A1 | 11/2003 | DeFelippis et al. |
| 2003/0220243 | A1 | 11/2003 | Glaesner et al. |
| 2003/0220255 | A1 | 11/2003 | Knudsen et al. |
| 2004/0156835 | A1 | 8/2004 | Imoto et al. |
| 2004/0164023 | A1* | 8/2004 | Christensen et al. ........ 210/649 |
| 2004/0248782 | A1 | 12/2004 | Bridon et al. |
| 2006/0084605 | A1 | 4/2006 | Engelund et al. |
| 2006/0287221 | A1 | 12/2006 | Knudsen et al. |

FOREIGN PATENT DOCUMENTS

| CA | 2306024 | 4/1999 |
| CA | 2527743 | 12/2004 |
| EP | 0431679 | 11/1990 |
| EP | 0438767 | 12/1990 |
| EP | 699687 | 8/1995 |
| EP | 0708179 | 4/1996 |
| EP | 0708179 A2 | 4/1996 |
| EP | 747390 | 12/1996 |
| EP | 0926159 | 6/1999 |
| EP | 1329462 | 10/2001 |
| EP | 1424077 | 5/2002 |
| EP | 1344533 | 9/2003 |

(Continued)

OTHER PUBLICATIONS

Bailey et al. The Kinetics of Enzyme-Catalysed Reactions Biochemical Engineering Fundamentals, 2nd Ed., pp. 129-148 (1986).
Chou, J. Z. et al., Journal of Pharmaceutical Sciences, A Radioimmunoassay for LY315902, an Analog of Glucagon-Like Insulinotropic Pepride, and its Application in the Study of Canine Pharmacokinetics, vol. 86(7), pp. 768-773 (1997).
D. Voet and J.G. Voet, Biochem, 2nd Ed., pp. 235-241 (1995).
D.E. Smilek et al., Proc Natl Acad Sci USA, vol. 88, pp. 9633-9637, (1991).
Entry for Glycerin in Drugs.Com (www.drugs.com/ppa/glycerin-glycerol.html), Printed Aug. 4, 2009.
European Pharmacopoeia, 2007, vol. 1, p. 730, Council of Europe-Strasbourg.

(Continued)

*Primary Examiner* — Christina Bradley
(74) *Attorney, Agent, or Firm* — Rosemarie R. Wilk-Orescan

(57) ABSTRACT

Stable pharmaceutical composition comprising insulinotropic peptide.

14 Claims, 20 Drawing Sheets

(56) References Cited

FOREIGN PATENT DOCUMENTS

| | | |
|---|---|---|
| EP | 1396499 | 3/2004 |
| EP | 722492 | 3/2005 |
| JP | 10101696 | 4/1998 |
| JP | 2000-510813 | 8/2000 |
| JP | 2001-525371 | 12/2001 |
| JP | 2002-504908 | 2/2002 |
| JP | 2002-508332 | 3/2002 |
| JP | 2002-524514 | 8/2002 |
| JP | 2002532557 | 10/2002 |
| JP | 2003-503356 | 1/2003 |
| JP | 2003519195 | 6/2003 |
| JP | 2004-518756 | 6/2004 |
| PA | 200101010 | 6/2001 |
| RU | 2180218 | 3/2002 |
| WO | WO9000200 | 1/1990 |
| WO | WO9219260 | 11/1992 |
| WO | 9318785 | 9/1993 |
| WO | WO9323010 | 11/1993 |
| WO | WO9522560 | 2/1995 |
| WO | 9505848 | 3/1995 |
| WO | 9510605 | 4/1995 |
| WO | WO9510605 | 4/1995 |
| WO | WO9513825 | 5/1995 |
| WO | WO9620005 | 7/1996 |
| WO | 9624369 | 8/1996 |
| WO | WO9638469 | 12/1996 |
| WO | WO9808871 | 3/1998 |
| WO | WO9831386 | 7/1998 |
| WO | 9856406 | 12/1998 |
| WO | WO9916417 | 4/1999 |
| WO | WO9921889 | 5/1999 |
| WO | 9929336 | 6/1999 |
| WO | WO9930731 | 6/1999 |
| WO | WO9943341 | 9/1999 |
| WO | WO9943706 | 9/1999 |
| WO | WO9943707 | 9/1999 |
| WO | WO0015224 | 3/2000 |
| WO | 0037098 A1 | 6/2000 |
| WO | WO0041546 | 7/2000 |
| WO | WO0055119 | 9/2000 |
| WO | WO 01/00223 | 1/2001 |
| WO | WO0143762 | 6/2001 |
| WO | 0151071 | 7/2001 |
| WO | WO0149314 | 7/2001 |
| WO | WO0152937 | 7/2001 |
| WO | 0155213 | 8/2001 |
| WO | WO 01/77141 | 10/2001 |
| WO | WO0267989 | 1/2002 |
| WO | 0247716 | 6/2002 |
| WO | WO0247715 | 6/2002 |
| WO | WO0248183 | 6/2002 |
| WO | WO 02/069994 | 9/2002 |
| WO | 02098445 | 12/2002 |
| WO | 03/002136 | 1/2003 |
| WO | WO03013589 | 2/2003 |
| WO | WO03020201 | 3/2003 |
| WO | 03035099 | 5/2003 |
| WO | 2004029076 | 4/2004 |
| WO | 2004/055213 A1 | 7/2004 |
| WO | WO2004105781 | 12/2004 |
| WO | WO2005000222 | 1/2005 |
| WO | WO 2005/046716 | 5/2005 |
| WO | 2006025882 | 3/2006 |

OTHER PUBLICATIONS

G.F. Stamper et al., "Accelerated Stability Testing of Proteins and Peptides: PH-Stability Profile of Insulinotropin Using Traditional Arrheneius and Non-Linear Fitting Analysis", Drug Development and Industrial Pharmacy, 1995, vol. 21, No. 13, pp. 1503-1511.
H. Qi et al., "Stability and Stabilization of Insulinotropin in a Dextran Formulation", PDA Journal of Pharmaceutical Science & Technology, vol. 49, No. 6, Nov.-Dec. 1995, pp. 289-293.
H.J.C. Berendsen, A Glimpse of the Holy Grail, Science, vol. 282, pp. 642-643 (1998).
http://www.copewithcytokines.de/cope.cgi?key=insulinotropin; (Host Ibelgauft's Cope: Cytokines & Cells Online Pathfinder Encyclopedia; Insulinotropin).
http://www.Copewithcytokineslde/cope.cgi?key=glp%2dl; (Host Ibelgauft's Cope: Cytokines & Cells Online Pathfinder Encyclopedia; GLP-1).
http://www.fermantas.com/techinfo/appendix/appendixtables1.htm, 'Temperature Dependence of the pH for Commonly Used Buffers' + 'Temperature Dependence of the pH of 50 mm Tris-HCl Solutions'.
Larsen, P.J. et al., Systemic Administration of the Logn Acting GLP-1, Diabetes, vol. 50, 2530-9,2000.
Malendowicz, L.K. et al., "Preproglucagon Derived Peptides and Thyrotropin (TSH) Secretion in the Rat: Robust and Sustained Lowering of Blood TSH Levels in Extendin-4 Injected Animals", International Journal of Molecular Medicine, vol. 10, pp. 327-331 (2002).
N. Good et al., "Hydrogen Ion Buffers for Biological Research", Biochemistry, 1966, vol. 5, No. 2, pp. 467-477.
Rudinger, IN: Peptide Hormones, JA Parsons, Ed., pp. 1-7 (1976).
S.E. Bondos & A. Bicknell, Detection and Prevention of Protein Aggregation Before During and After Purification, Analytical Biochemistry, 2003, 223-231, vol. 316, Academic Press.
Shinotesuto, Patentabstracts of Japan, of JP10101696.
Sigma, http://www.sigma-genosys.com/peptide design.asp (Accessed Dec. 16, 2004).
Singh, S. et al. AAPS Pharmscitech, vol. 4(3), pp. 334-342 (2003).
Skovgaard et al., "Using Evolutionary Information and Ancestral Sequences to Understand the Sequence-Function Relationship in GLP-1 Agonists," J. Mol. Bio., 2006, vol. 363, pp. 977-988.
Tsoka et al, Selective Flocculation ands Precipitation for the Improvement of Virus-Like Particle Recovery From Yeast Homogenate, Biotechnol Prog. vol. 16(4), pp. 661-667 (2000).
W.S. Messer, Vasopressin and Oxytocin, http://www.neurosci.pharm.utoldeo.edu/mbc3320/vasopressin.htm.
Non-Final Office Action in U.S. Appl. No. 10/185,923, filed Jun. 27, 2002, Inventors: Flink et al. Sent Mar. 10, 2006.
Non-Final Office Action in U.S. Appl. No. 10/185,923, filed Jun. 27, 2002, Inventors: Flink et al. Sent Oct. 9, 2007.
Non-Final Office Action in U.S. Appl. No. 11/786,095, filed Apr. 11, 2007, Inventors: Flink et al. Sent Feb. 24, 2009.
Non-Final Office Action in U.S. Appl. No. 12/343,722, filed Dec. 24, 2008, Inventors: Flink et al. Sent May 22, 2009.
Non-Final Office Action in U.S. Appl. No. 10/719,601, filed Nov. 21, 2003, Inventors: Markussen et al. Sent Mar. 4, 2005.
Non-Final Office Action in U.S. Appl. No. 11/220,266, filed Sep. 6, 2005, Inventors: Markussen et al. Sent Sep. 14, 2006.
Non-Final Office Action in U.S. Appl. No. 11/220,266, filed Sep. 6, 2005, Inventors: Markussen et al. Sent Feb. 11, 2008.
Non-Final Office Action in U.S. Appl. No. 11/220,266, filed Sep. 6, 2005, Inventors: Markussen et al. Sent Oct. 1, 2007.
Non-Final Office Action in U.S. Appl. No. 11/435,977, filed May 17, 2006, Inventors: Pedersen et al. Sent Dec. 2, 2008.
Non-Final Office Action in U.S. Appl. No. 11/290,635, filed Nov. 30, 2005, Inventors: Juul-Mortensen et al. Sent Feb. 2, 2007.
Non-Final Office Action Dated Dec. 9, 2009 in U.S. Appl. No. 12/184,531, filed Aug. 1, 2008 by Juul-Mortensen.
Non-Final Office Action in U.S. Appl. No. 11/290,634, filed Nov. 30, 2005, Inventors: Juul-Mortensen et al. Sent Jun. 30, 2008.
Non-Final Office Action in U.S. Appl. No. 11/290,634, filed Nov. 30, 2005, Inventors: Juul-Mortensen et al. Sent Nov. 9, 2007.
Non-Final Office Action in U.S. Appl. No. 11/365,274, filed Mar. 1, 2006, Inventors: Schlein et al. Sent Aug. 20, 2007.
Non-Final Office Action in U.S. Appl. No. 11/365,274, filed Mar. 1, 2006, Inventors: Schlein et al. Sent Feb. 5, 2007.
Non-Final Office Action in U.S. Appl. No. 11/365,274, filed Mar. 1, 2006, Inventors: Schlein et al. Sent Jan. 28, 2009.
Final Office Action in U.S. Appl. No. 10/185,923, filed Jun. 27, 2002, Inventors: Flink et al. Sent Dec. 12, 2006.
Final Office Action in U.S. Appl. No. 10/185,923, filed Jun. 27, 2002, Inventors: Flink et al. Sent Jun. 14, 2005.
Final Office Action in U.S. Appl. No. 10/185,923, filed Jun. 27, 2002, Inventors: Flink et al. Sent Jun. 30, 2008.
Final Office Action in U.S. Appl. No. 11/786,095, filed Apr. 11, 2007, Inventors: Flink et al. Sent Nov. 24, 2009.

(56) References Cited

OTHER PUBLICATIONS

Final Office Action in U.S. Appl. No. 12/343,722, filed Dec. 24, 2008, Inventors: Flink et al. Sent Feb. 18, 2009.
Final Office Action in U.S. Appl. No. 11/435,977, filed May 17, 2006, Inventors: Pedersen et al. Sent Jun. 25, 2009.
Final Office Action in U.S. Appl. No. 11/290,635, filed Nov. 30, 2005, Inventors: Juul-Mortensen Sent Sep. 5, 2007.
Final Office Action in U.S. Appl. No. 11/365,274, filed Mar. 1, 2006, Inventors: Schlein et al. Sent Apr. 4, 2008.
Final Office Action in U.S. Appl. No. 11/365,274, filed Mar. 1, 2006, Inventors: Schlein et al. Sent Aug. 12, 2009.
Brittain, Harry G., Buffers, Buffering Agents, and Ionic Equilibria, Encyclopedia of Pharmaceutical Technology, p. 385, 2007.
Blundell, T.L., Springer Verlag, 1983, pp. 37-55.
Eli Lilly & Co., Humalog Lispro Injection, USP Product Information Dated Feb. 11, 2010.
European Pharmacopoeia, 3rd Edition, 2.2.3, 1997, pp. 17-18, Council of Europe-Strasbourg.
Frokjaer & Hovgaard, Pharmaceutical Formulation Development of, 2000, pp. 145-148 & 150-151.
Further Experimental Data Dated Jun. 22, 2009.
Gonzales, Johnny C., Declaration of (Including Curriculum Vita) Dated Nov. 1, 2010.
Knudsen, L.B. et al., Potent Derivatives of Glucogon-Like Peptide-1, Journal of Medicinal Chemistry, 2000, vol. 43, pp. 1664-1669.
Kristensen, H.G., Almen Farmaci, 2000, pp. 273-274, 281.
Lund, Walter, Editor, The Pharmaceutical Codex, 12th Edition, 1994, The Pharmaceutical Press, London, pp. 98-99.
Mack Publishing Co., Remington's Pharmaceutical Sciences, 16th Edition, 1980, Pt. 79, p. 1406.
Mack Publishing Co., Remington's Pharmaceutical Sciences, 18th Edition, 1990, Chapter 84, pp. 1545-1550.
Martin A. et al., Physical Pharmacy; Physical Chemical Principles in the Pharmaceutical Sciences, 1983, 3rd Edition, p. 232.
Senderoff, R.I. et al, Consideration of Conformational Transitions and Racemization during Process Development of Recombinant Glucagon-like Peptide-1, Journal of Pharmaceutical Sciences, 1998, 183-189, vol. 87—No. 2, American Chemical Society & American Pharm. Assc.
Sigma Product Information on Gly-Gly Buffer Dated Mar. 16, 2010.
Stenesh, J. Biochemistry, 1998, pp. 67-69.
United States Pharmacopoeia, 24th Edition, 1999, pp. 1977-1978.
Villanueva_Penacarril, M.L, Potent Glycognic Effect of GLP-1(7-36) Amide in Rat Skeletal Muscle, Diabetologia, 1994, vol. 37, pp. 1163-1166.
Wang & Hansen, Journal of Parenteral Science & Technology, 1988, vol. 42, pp. 4-26.
Wang et. al., Aggregation of Therapeutic Proteins, 2010, p. 241.
Weinstein, Sharon, Plumer's Principles & Practice of Intravenous, 2006, vol. 8 (8), pp. 124-128.
Duma et al., Pharmaceutical Dosage Forms: Parenteral Medications, vol. 1, 2nd Edition, p. 20, 1992.
International Search Report for International Application No. PCT/EP2005/055946 filed Nov. 14, 2005.
Siegel et al., "Biological activity of GLP-1-analogues with N-terminal modifications" Regulatory Peptides, 1999, vol. 79, pp. 93-102.
Mentlein et al., "Dipeptidyl-peptidase IV hydrolyses gastric inhibitory polypeptide, glucagon-like peptide-1(7-36)amide, peptide histidine methionine and is responsible for their degradation in human serum," European Journal of Biochemistry, 1993, vol. 214, pp. 829-835.
Naiki et al., "Fluorometric Determination of Amyloid Fibrils in Vitro Using the Fluorescent Dye, Thioflavine T." Analytical Biochemistry, 1989, vol. 177, No. 2, pp. 244-249.
LeVine III, Harry, "Quantification of B-Sheet Amyloid Fibril Structures With Thioflavin T," Methods in Enzymology, 1999, vol. 309, pp. 274-284.
Andersen et al., "Medium-Dependence of the Secondary Structure of Exendin-4 and Glucagon-Like-Peptide-1", Bioorganic & Medicinal Chemistry, 2002, vol. 10, pp. 79-85.
Clodfelter et al., "Effects of Non-Covalent Self-Association on the Subcutaneous Absorption of a Therapeutic Peptide", Pharmaceutical Research, 1998, vol. 15, No. 2, pp. 254-262.
U.S. Appl. No. 10/185,923, filed Jun. 27, 2002, Flink et al.
U.S. Appl. No. 11/786,095, filed Apr. 11, 2007, Flink et al.
U.S. Appl. No. 12/343,722, filed Dec. 24, 2008, Flink et al.
U.S. Appl. No. 12/785,861, filed May 24, 2010, Funk et al.
U.S. Appl. No. 10/719,601, filed Nov. 21, 2003, Markussen et al.
U.S. Appl. No. 11/220,266, filed Sep. 6, 2005, Markussen et al.
U.S. Appl. No. 11/435,977, filed May 17, 2006, Pedersen et al.
U.S. Appl. No. 11/290,635, filed Nov. 30, 2005, Juul-Mortensen.
U.S. Appl. No. 12/184,531, filed Aug. 1, 2008, Juul-Mortensen.
U.S. Appl. No. 11/290,634, filed Nov. 30, 2005, Juul-Mortensen et al.
U.S. Appl. No. 12/612,888, filed Nov. 5, 2009, Juul-Mortensen et al.
U.S. Appl. No. 11/365,274, filed Mar. 1, 2006, Schlein et al.
U.S. Appl. No. 12/752,634, filed Apr. 1, 2010, Schlein et al.
U.S. Appl. No. 11/667,040, filed May 3, 2007, Ludvigsen et al.
Nielsen et al. "Effecr of Environmental Factors on the Kinetics of Insulin Fibril Formation: Elucidation of the Molecular Mechanism." Biochemistry. vol. 40. pp. 6036-6046.
Cai-Hong Z et al. "Glucagon-like peptide-1 receptor: a novel therapeutic target for diabetes" Chinese Bulletin of Life Sciences. 2004. vol. 16(2) pp. 90-95.

* cited by examiner

SEQUENCE LISTING

```
<160> NUMBER OF SEQ ID NOS: 5

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 44
<212> TYPE: PRT
<213> ORGANISM: Artificial
<220> FEATURE:
<223> OTHER INFORMATION: ZP-10
<220> FEATURE:
<221> NAME/KEY: MOD_RES
<222> LOCATION: (44)..(44)
<223> OTHER INFORMATION: AMIDATION

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```

```
<210> SEQ ID NO 4
<211> LENGTH: 39
<212> TYPE: PRT
<213> ORGANISM: Artificial
<220> FEATURE:
<223> OTHER INFORMATION: synthetic compound
<220> FEATURE:
<221> NAME/KEY: MISC_FEATURE
<222> LOCATION: (20)..(20)
<223> OTHER INFORMATION: Lys is substituted
<220> FEATURE:
<221> NAME/KEY: MOD_RES
<222> LOCATION: (39)..(39)
<223> OTHER INFORMATION: AMIDATION

<400> SEQUENCE: 4

His Gly Glu Gly Thr Phe Thr Ser Asp Leu Ser Lys Gln Met Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial
<220> FEATURE:
<223> OTHER INFORMATION: synthetic compound
<220> FEATURE:
<221> NAME/KEY: MISC_FEATURE
<222> LOCATION: (32)..(32)
<223> OTHER INFORMATION: Lys is substituted
<220> FEATURE:
<221> NAME/KEY: MOD_RES
<222> LOCATION: (39)..(39)
<223> OTHER INFORMATION: AMIDATION

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Lys
            20                  25                  30

Ser Gly Ala Pro Pro Pro Ser
        35
```

STABLE FORMULATIONS OF PEPTIDES

CROSS-REFERENCE TO RELATED APPLICATIONS

This application is a divisional of U.S. application Ser. No. 11/667,040 filed Nov. 6, 2007, which is a National Stage filing of International Application No. PCT/EP2005/055946, filed Nov. 14, 2005, which claims priority from U.S. Application No. 60/629,115, filed Nov. 18, 2004, and U.S. Application No. 60/635,311, filed Dec. 10, 2004, and U.S. Application No. 60/682,724, fled May 19, 2005, and which also claims priority from Danish Patent Application No. PA 2004 01753, filed Nov. 12, 2004, and Danish Application No. PA 2004 01906, filed Dec. 8, 2004, and European Application No. 05104050.9, filed May 13, 2005, and European Application No. 05104172.1, filed May 18, 2005, and European Application No. PCT/EP2005/055916, filed Nov. 11, 2005.

FIELD OF THE INVENTION

The present invention relates to the field of pharmaceutical formulations. More specifically the invention pertains to shelf-stable pharmaceutical formulations comprising an insulinotropic peptide.

BACKGROUND OF THE INVENTION

Therapeutic peptides are widely used in medical practise. Pharmaceutical compositions of such therapeutic peptides are required to have a shelf life of several years in order to be suitable for common use. However, peptide compositions are inherently unstable due to sensitivity towards chemical and physical degradation. Chemical degradation involves change of covalent bonds, such as oxidation, hydrolysis, racemization or crosslinking. Physical degradation involves conformational changes relative to the native structure of the peptide, which may lead to aggregation, precipitation or adsorption to surfaces.

Glucagon has been used for decades in medical practise within diabetes and several glucagon-like peptides are being developed for various therapeutic indications. The preproglucagon gene encodes glucagon as well as glucagon-like peptide 1 (GLP-1) and glucagon-like peptide 2 (GLP-2). GLP-1 analogs and derivatives as well as the homologous lizard peptide, exendin-4, are being developed for the treatment of hyperglycemia within type 2 diabetes. GLP-2 are potentially useful in the treatment of gastrointestinal diseases. However, all these peptides encompassing 29-39 amino acids have a high degree of homology and they share a number of properties, notably their tendency to aggregate and formation of insoluble fibrils. This property seems to encompass a transition from a predominant alpha-helix conformation to beta-sheets (Blundell T. L. (1983) The conformation of glucagon. In: Lefébvre P. J. (Ed) Glucagon I. Springer Verlag, pp 37-55, Senderoff R. I. et al., J. Pharm. Sci. 87 (1998)183-189, WO 01/55213). Aggregation of the glucagon-like peptides are mainly seen when solutions of the peptides are stirred or shaken, at the interface between solution and gas phase (air), and at contact with hydrophobic surfaces such as Teflon®.

WO 01/77141 discloses heat treatment of $Arg^{34}$-GLP-1(7-37) at elevated temperatures for less than 30 seconds. WO 04/55213 discloses microfiltration of $Arg^{34}$-GLP-1(7-37) at pH 9.5. WO 01/55213 discloses treatment of $Val^{8}$-GLP-1(7-37) at pH 12.3 for 10 minutes at room temperature. WO 03/35099 discloses the preparation of zinc crystals of GLP-1 at alkaline pH.

Thus, various treatments and addition of excipients must often be applied to pharmaceutical compositions of the glucagon-like peptides in order to improve their stability. Shelf life of liquid parenteral formulations of these peptides must be at least a year, preferably longer. The in-use period where the product may be transported and shaken daily at ambient temperature preferably should be several weeks. Thus, there is a need for pharmaceutical compositions of glucagon-like peptides which have improved stability.

DEFINITIONS

Figure 1:
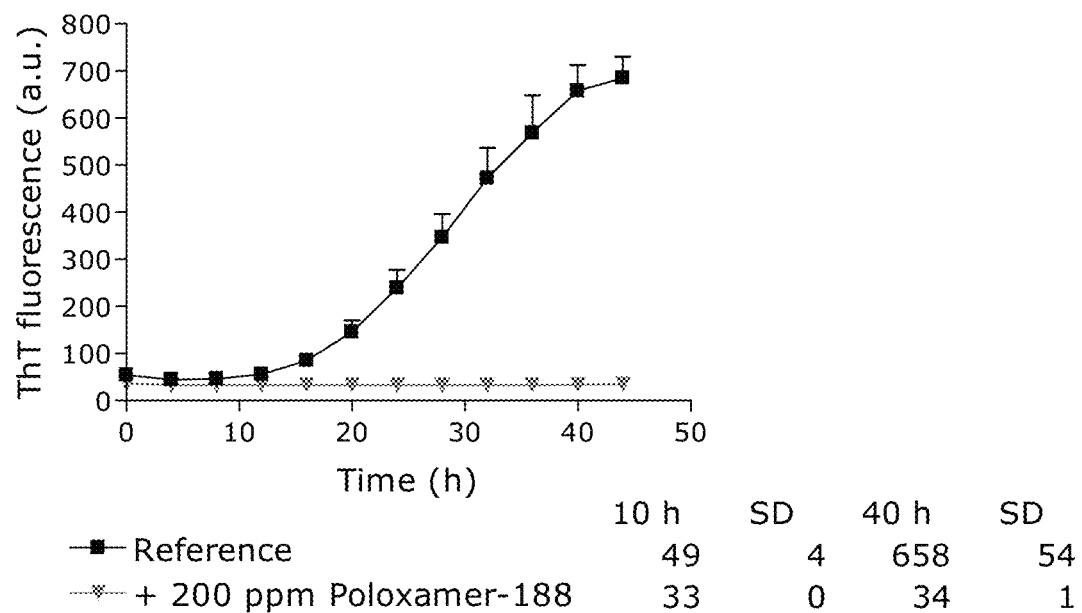
FIG. 1. Both samples contain a formulation of 1.2 mM Liraglutide, 14 mg/ml propylene glycol, 40 mM phenol, 10 mM NaCl, pH 7.7. Poloxamer-188 is added to a final concentration of 200 ppm in one sample.

The following is a detailed definition of the terms used in the specification.

The term "effective amount" as used herein means a dosage which is sufficient in order for the treatment of the patient to be effective compared with no treatment.

The term "medicament" as used herein means a pharmaceutical composition suitable for administration of the pharmaceutically active compounds to a patient.

The term "pharmaceutical composition" as used herein means a product comprising an active compound or a salt thereof together with pharmaceutical excipients such as buffer, preservative and tonicity modifier, said pharmaceutical composition being useful for treating, preventing or reducing the severity of a disease or disorder by administration of said pharmaceutical composition to a person. Thus a pharmaceutical composition is also known in the art as a pharmaceutical formulation. It is to be understood that pH of a pharmaceutical composition which is to be reconstituted is the pH value which is measured on the reconstituted composition produced by reconstitution in the prescribed reconstitution liquid at room temperature.

The term "shelf-stable pharmaceutical composition" as used herein means a pharmaceutical composition which is stable for at least the period which is required by regulatory agencies in connection with therapeutic proteins. Preferably, a shelf-stable pharmaceutical composition is stable for at least one year at 5° C. Stability includes chemical stability as well as physical stability.

The term "pharmaceutically acceptable" as used herein means suited for normal pharmaceutical applications, i.e. giving rise to no adverse events in patients etc.

The term "buffer" as used herein refers to a chemical compound in a pharmaceutical composition that reduces the tendency of pH of the composition to change over time as would otherwise occur due to chemical reactions. Buffers include chemicals such as sodium phosphate, TRIS, glycine and sodium citrate.

The term "preservative" as used herein refers to a chemical compound which is added to a pharmaceutical composition to prevent or delay microbial activity (growth and metabolism). Examples of pharmaceutically acceptable preservatives are phenol, m-cresol and a mixture of phenol and m-cresol.

The term "isotonicity agent" as used refers to a chemical compound in a pharmaceutical composition that serves to modify the osmotic pressure of the pharmaceutical composition so that the osmotic pressure becomes closer to that of human plasma. Isotonicity agents include NaCl, glycerol, mannitol etc.

The term "stabilizer" as used herein refers to chemicals added to peptide containing pharmaceutical compositions in order to stabilize the peptide, i.e. to increase the shelf life and/or in-ude time of such compositions. Examples of stabilizers used in pharmaceutical formulations are L-glycine, L-histidine, arginine, polyethylene glycol, and carboxymethylcellulose.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder, and prevention of the disease, condition or disorder.

The term "prevention of a disease" as used herein is defined as the management and care of an individual at risk of developing the disease prior to the clinical onset of the disease. The purpose of prevention is to combat the development of the disease, condition or disorder, and includes the administration of the active compounds to prevent or delay the onset of the symptoms or complications and to prevent or delay the development of related diseases, conditions or disorders.

The term "analogue" as used herein referring to a peptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. In one embodiment an analogue comprises less than 6 modifications (substitutions, deletions, additions) relative to the native peptide. In another embodiment an analogue comprises less than 5 modifications (substitutions, deletions, additions) relative to the native peptide. In another embodiment an analogue comprises less than 4 modifications (substitutions, deletions, additions) relative to the native peptide. In another embodiment an analogue comprises less than 3 modifications (substitutions, deletions, additions) relative to the native peptide. In another embodiment an analogue comprises less than 2 modifications (substitutions, deletions, additions) relative to the native peptide. In another embodiment an analogue comprises only a single modification (substitutions, deletions, additions) relative to the native peptide.

The term "derivative" as used herein in relation to a parent peptide means a chemically modified parent protein or an analogue thereof, wherein at least one substituent is not present in the parent protein or an analogue thereof, i.e. a parent protein which has been covalently modified. Typical modifications are amides, carbohydrates, alkyl groups, acyl groups, esters, PEGylations and the like.

The term "GLP-1 compound" as used herein means GLP-1(7-37) (SEQ ID NO. 1), insulinotropic analogue thereof and insulinotropic derivatives thereof. Non-limiting examples of GLP-1 analogues are GLP-1(7-36) amide, $Arg^{34}$-GLP-1(7-37), $Gly^8$-GLP-1(7-37), $Val^8$-GLP-1(7-36)-amide and $Val^8 Asp^{22}$-GLP-1(7-37). Non-limiting examples of GLP-1 derivatives are desamino-$His^7$, $Arg^{26}$, $Lys^{34}(N^\epsilon$-($\gamma$-Glu($N^\alpha$-hexadecanoyl)))-GLP-1(7-37), desamino-$His^7$, $Arg^{26}$, $Lys^{34}$ ($N^\epsilon$-octanoyl)-GLP-1(7-37), $Arg^{26,34}$, $Lys^{38}(N^\epsilon$-($\omega$-carboxypentadecanoyl))-GLP-1(7-38), $Arg^{26,34}$, $Lys^{36}(N^\epsilon$-($\gamma$-Glu($N^\alpha$-hexadecanoyl)))-GLP-1(7-36) and $Arg^{34}$, $Lys^{26}(N^\epsilon$-($\gamma$-Glu($N^\alpha$-hexadecanoyl)))-GLP-1(7-37).

The term "dipeptidyl aminopeptidase IV protected" as used herein means a compound, e.g. a GLP-1 analogue, which is more resistant to dipeptidyl aminopeptidase IV (DPP-IV) than the native compound, e.g. GLP-1(7-37). Resistance of a GLP-1 compound towards degradation by dipeptidyl aminopeptidase IV is determined by the following degradation assay:

Aliquots of the GLP-1 compound (5 nmol) are incubated at 37° C. with 1 μL of purified dipeptidyl aminopeptidase IV corresponding to an enzymatic activity of 5 mU for 10-180 minutes in 100 μL of 0.1 M triethylamine-HCl buffer, pH 7.4. Enzymatic reactions are terminated by the addition of 5 μL of 10% trifluoroacetic acid, and the peptide degradation products are separated and quantified using HPLC analysis. One method for performing this analysis is: The mixtures are applied onto a Vydac C18 widepore (30 nm pores, 5 μm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a GLP-1 compound by dipeptidyl aminopeptidase IV is estimated at incubation times which result in less than 10% of the GLP-1 compound being hydrolysed.

The term "insulinotropic" as used herein referring to a peptide or a compound means the ability to stimulate secretion of insulin in response to an increased plasma glucose level. Insulinotropic peptides and compounds are agonists of the GLP-1 receptor. The insulinotropic property of a compound may be determined by in vitro or in vivo assays known in the art. The following in vitro assay may be used to determine the insulinotropic nature of a compound such as a peptide. Preferably insulinotropic compounds exhibit an $EC_{50}$ value in below assay of less than 5 nM, even more preferably EC50 values less than 500 pM.

Baby hamster kidney (BHK) cells expressing the cloned human GLP-1 receptor (BHK 467-12A) are grown in DMEM media with the addition of 100 IU/mL penicillin, 100 μL/mL streptomycin, 10% foetal calf serum and 1 mg/mL Geneticin G-418 (Life Technologies). Plasma membranes are prepared by homogenization in buffer (10 mM Tris-HCl, 30 mM NaCl and 1 mM dithiothreitol, pH 7.4, containing, in addition, 5 mg/mL leupeptin (Sigma), 5 mg/L pepstatin (Sigma), 100 mg/L bacitracin (Sigma), and 16 mg/L aprotinin (Calbiochem-Novabiochem, La Jolla, Calif.)). The homogenate was centrifuged on top of a layer of 41% W7v sucrose. The white band between the two layers was diluted in buffer and centrifuged. Plasma membranes were stored at −80° C. until used.

The functional receptor assay is carried out by measuring cAMP as a response to stimulation by the insulinotropic peptide or insulinotropic compound. Incubations are carried out in 96-well microtiter plates in a total volume of 140 mL and with the following final concentrations: 50 mM Tris-HCl, 1 mM EGTA, 1.5 mM $MgSO_4$, 1.7 mM ATP, 20 mM GTP, 2 mM 3-isobutyl-1-methylxanthine (IBMX), 0.01% w/v Tween-20, pH 7.4. Compounds are dissolved and diluted in buffer. GTP is freshly prepared for each experiment: 2.5 pg of membrane is added to each well and the mixture is incubated for 90 min at room temperature in the dark with shaking. The reaction is stopped by the addition of 25 mL 0.5 M HCl. Formed cAMP is measured by a scintillation proximity assay (RPA 542, Amersham, UK). A dose-response curves is plotted for the compound and the $EC_{50}$ value is calculated using GraphPad Prism software.

The term "prodrug of an insulinotropic compound" as used herein means a chemically modified compound which following administration to the patient is converted to an insulinotropic compound. Such prodrugs are typically amino acid extended versions or esters of an insulinotropic compound.

The term "exendin-4 compound" as used herein is defined as exendin-4(1-39) (SEQ ID NO. 2), insulinotropic fragments thereof, insulinotropic analogs thereof and insulinotropic derivatives thereof. Insulinotropic fragments of exendin-4 are insulinotropic peptides for which the entire sequence can be found in the sequence of exendin-4 (SEQ ID NO. 2) and where at least one terminal amino acid has been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogs of exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. An example of an insulinotropic analog of exendin-4(1-39) is $Ser^2Asp^3$-exendin-4(1-39) wherein the amino acid residues in position 2 and 3 have been replaced with serine and aspartic acid, respectively (this particular analog also being known in the art as exendin-3). Insulinotropic derivatives of exendin-4(1-39) and analogs thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups, esters and lipophilic substituents. An example of an insulinotropic derivatives of exendin-4(1-39) and analogs thereof is $Tyr^{31}$-exendin-4(1-31)-amide.

The term "stable exendin-4 compound" as used herein means a chemically modified exendin-4(1-39), i.e. an analogue or a derivative which exhibits an in vivo plasma elimination half-life of at least 10 hours in man, as determined by the method described under the definition of "stable GLP-1 compound".

The term "dipeptidyl aminopeptidase IV protected exendin-4 compound" as used herein means an exendin-4 compound which is more resistant towards the plasma peptidase dipeptidyl aminopeptidase IV (DPP-IV) than exendin-4 (SEQ ID NO. 2), as determined by the assay described under the definition of dipeptidyl aminopeptidase IV protected GLP-1 compound.

The term "isoelectric point" as used herein means the pH value where the overall net charge of a macromolecule such as a peptide is zero. In peptides there may be several charged groups, and at the isoelectric point the sum of all these charges is zero. At a pH above the isoelectric point the overall net charge of the peptide will be negative, whereas at pH values below the isoelectric point the overall net charge of the peptide will be positive.

The term "reconstituted" as used herein referring to a pharmaceutical composition means an aqueous composition which has been formed by the addition of water to a solid material comprising the active pharmaceutical ingredient. Pharmaceutical compositions for reconstitution are applied where a liquid composition with acceptable shelf-life cannot be produced. An example of a reconstituted pharmaceutical composition is the solution which results when adding water to a freeze dried composition. The solution is often for parenteral administration and thus water for injection is typically used for reconstituting the solid material.

The term "about" as used herein means in reasonable vicinity of the stated numerical value, such as plus or minus 10%.

DESCRIPTION OF THE INVENTION

In a first aspect the present invention relates to a shelf-stable pharmaceutical composition comprising an insulinotropic peptide, a pharmaceutically acceptable preservative, a poloxamer or polysorbate 20 surfactant at a concentration of from about 10 mg/L to about 400 mg/L, and optionally a pharmaceutically acceptable tonicity modifier, where said composition has a pH that is in the range from about 7.0 to about 8.5.

In one embodiment the concentration of surfactant is from about 20 mg/L to about 300 mg/L.

In another embodiment the concentration of surfactant is from about 50 mg/L to about 200 mg/L.

In another embodiment the concentration of surfactant is from about 10 mg/L to about 200 mg/L.

In another embodiment the concentration of surfactant is from about 50 mg/L to about 400 mg/L.

In another embodiment the concentration of surfactant is from about 50 mg/L to about 300 mg/L.

In another embodiment the surfactant is poloxamer 188.

In another embodiment the surfactant is selected from the group consisting of poloxamer 407, poloxamer 124, poloxamer 181, poloxamer 182, poloxamer 237, poloxamer 331 and poloxamer 338.

In another embodiment the surfactant is polysorbate 20.

In another embodiment of the invention the pharmaceutical composition comprises two different surfactants.

In another embodiment of the invention the pharmaceutical composition comprises two different surfactants wherein at least one surfactant is a non-ionic surfactant.

In another embodiment of the invention the pharmaceutical composition comprises two different surfactants wherein the two different surfactants are both non-ionic surfactants.

In another embodiment of the invention the pharmaceutical composition comprises two different surfactants wherein all surfactants are non-ionic surfactants.

In another embodiment of the invention the pharmaceutical composition comprises poloxamer 188 and polysorbate 20.

In another embodiment of the invention the pharmaceutical composition has a pH in the range from about 7.4 to about 8.0.

In another embodiment of the invention the pharmaceutical composition has a pH in the range from about 7.4 to about 8.5.

In another embodiment of the invention the pharmaceutical composition has a pH in the range from about 7.7 to about 8.2.

In another embodiment of the invention the pharmaceutical composition comprises a buffer which is a phosphate buffer.

In another embodiment of the invention the pharmaceutical composition comprises a buffer which is a zwitterionic buffer.

In another embodiment of the invention the pharmaceutical composition comprises a buffer which is selected from the group consisting of glycyl-glycine, TRIS, bicine, HEPES, MOBS, MOPS, TES and mixtures thereof.

In another embodiment of the invention the pharmaceutical composition comprises a tonicity modifier selected from the group consisting of glycerol, propylene glycol and mannitol.

In another embodiment of the invention the pharmaceutical composition the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, thiomerosal and mixtures thereof.

In another embodiment of the invention the pharmaceutical composition comprises an insulinotropic peptide which is a DPP-IV protected peptide.

In another embodiment of the invention the pharmaceutical composition the insulinotropic peptide comprises a lipophilic substituent selected from the group consisting of $CH_3(CH_2)_nCO-$ wherein n is 4 to 38, and $HOOC(CH_2)_mCO-$ wherein m is from 4 to 38.

In another embodiment of the invention the pharmaceutical composition the insulinotropic peptide is acylated GLP-1 or an acylated GLP-1 analogue.

In another embodiment of the invention the pharmaceutical composition comprises an insulinotropic peptide which is an acylated GLP-1 analogue wherein said GLP-1 analogue is selected from the group consisting of $Arg^{34}$-GLP-1(7-37), $Gly^8$-GLP-1(7-36)-amide, $Gly^8$-GLP-1(7-37), $Val^8$-GLP-1(7-36)-amide, $Val^8$-GLP-1(7-37), $Aib^8$-GLP-1(7-36)-amide, $Aib^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{19}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}Ile^{33}$-GLP-1(7-37), $Val^8Trp^{16}Glu^{22}Ile^{33}$-GLP-1(7-37), $Val^8Glu^{22}Val^{25}Ile^{33}$-GLP-1(7-37), $Val^8Trp^{16}Glu^{22}Val^{25}$-GLP-1(7-37), and analogues thereof.

In another embodiment of the invention the pharmaceutical composition the insulinotropic peptide is $Arg^{34}$, $Lys^{26}(N^\epsilon$-$(\gamma$-Glu($N^\alpha$-hexadecanoyl)))-GLP-1(7-37).

In another embodiment of the invention the concentration of said insulinotropic peptide is in the range from about 0.1 mg/ml to about 25 mg/ml, in the range from about 1 mg/ml to about 25 mg/ml, in the range from about 2 mg/ml to about 15 mg/ml, in the range from about 3 mg/ml to about 10 mg/ml, or in the range from about 5 mg/ml to about 8 mg/ml.

In another embodiment of the invention the insulinotropic peptide is exendin-4 or ZP-10, i.e. HGEGTFTSDL-SKQMEEEAVRLFIEWLKNGGPSSGAPPSKKKKKK-NH2.

In another embodiment of the invention the pharmaceutical composition the insulinotropic peptide is acylated exendin-4 or an acylated exendin-4 analogue.

In another embodiment of the invention the pharmaceutical composition the insulinotropic peptide is [N-epsilon(17-carboxyheptadecanoic acid)20 exendin-4(1-39)-amide or
N-epsilon32-(17-carboxy-heptadecanoyl)[Lys32]exendin-4 (1-39)amide

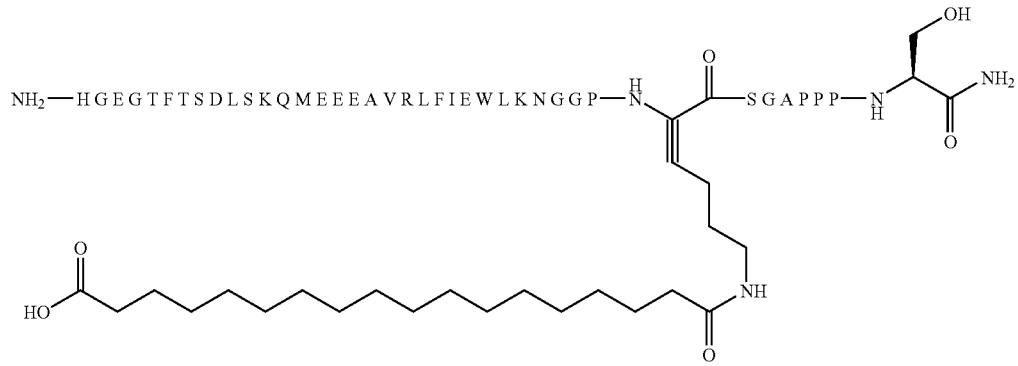

In another embodiment of the invention the pharmaceutical composition the concentration of the insulinotropic peptide in the pharmaceutical composition is from about 5 µg/mL to about 10 mg/mL, from about 5 µg/mL to about 5 mg/mL, from about 5 µg/mL to about 5 mg/mL, from about 0.1 mg/mL to about 3 mg/mL, or from about 0.2 mg/mL to about 1 mg/mL.

In another aspect the present invention relates to a method for preparation of a pharmaceutical composition according to the invention, said method comprising dissolving said insulinotropic peptide and admixing the preservative and tonicity modifier.

The present invention also relates to a method for preparation of a stable solution of a GLP-1 compound, which method comprises heating a solution of said GLP-1 compound at alkaline pH to a temperature above 40° C. for at least 5 minutes. Concentrations of the GLP-1 compound during the heat treatment is generally preferred to be in the range from 10 g/L to 100 g/L. The GLP-1 compound may be dissolved in an aqueous solution having the final temperature, or it may be dissolved in aqueous solution having room temperature followed by heating to the appropriate temperature for the specified time.

It has been shown that the physical stability of liraglutide was significantly improved as the temperature of heat treatment was increased (22 to 80° C.). For temperatures of 60 and 80° C., time of heat treatment was shown to have a strong influence on the physical stability of liraglutide, as 120 minutes of heat treatment showed to improve the physical stability significantly in comparison to 1 minute of heat treatment. It has also been shown that the physical stability of liraglutide was significantly improved by increasing the temperature from 22 to 50-80° C. at pH 9-10 (cn.f. examples). For all temperatures, time of heat treatment was shown to have an influence on the physical stability of liraglutide, as 15 to 20 minutes of heat treatment showed to improve the physical stability significantly compared to 1 minute of heat treatment. Optimal conditions for heat treatment to dissolve fibril germs appear to be 3-20 minutes at pH 9-10.5 and 70-85° C. In production scale, this could be performed using common methods for fast heating and cooling of large volumes by heat exchangers.

In another aspect the present invention relates to a method for preparation of a stable solution of a GLP-1 compound, which method comprises heating a solution of said GLP-1 compound having a pH between pH 8.0 to pH 10.5 to a temperature between 50° C. and 80° C. for a period of time which is between 3 minutes and 180 minutes.

In one embodiment the present invention relates to a method for preparation of a stable solution of a GLP-1 compound, which method comprises heating a solution of said GLP-1 compound having a pH between pH 8.0 to pH 10.0 to a temperature between 50° C. and 80° C. for a period of time which is between 3 minutes and 180 minutes.

In another embodiment the present invention relates to a method for preparation of a stable solution of a GLP-1 compound, which method comprises heating a solution of said GLP-1 compound having a pH between pH 8.0 to pH 10.0 to a temperature between 50° C. and 80° C. for a period of time which is between 3 minutes and 120 minutes.

In another embodiment the temperature is between 60° C. and 80° C. for a period of time which is between 5 minutes and 15 minutes.

In another embodiment the temperature is between 60° C. and 80° C. for a period of time which is between 1 minute and 15 minutes.

In another embodiment the temperature is between 60° C. and 80° C. for a period of time which is between 3 minutes and 30 minutes.

In another embodiment the temperature is between 60° C. and 80° C. for a period of time which is between 5 minutes and 30 minutes.

In another embodiment the present invention relates to a method for preparation of a stable solution of exendin-4, which method comprises heating a solution of exendin-4 having a pH between pH 8.0 to pH 10.0 to a temperature between 50° C. and 80° C. for a period of time which is between 3 minutes and 120 minutes.

In another embodiment the present invention relates to a method for preparation of a stable solution of Aib$^{8,35}$-GLP-1 (7-36)-amide, which method comprises heating a solution of Aib$^{8,35}$-GLP-1(7-36)-amide having a pH between pH 8.0 to pH 10.0 to a temperature between 50° C. and 80° C. for a period of time which is between 3 minutes and 120 minutes.

In another embodiment the GLP-1 compound is Arg$^{34}$, Lys$^{26}$(N$^\epsilon$-(γ-Glu(N$^\alpha$-hexadecanoyl)))-GLP-1(7-37).

In another aspect the present invention relates to a method for preparation of a shelf-stable pharmaceutical composition of a GLP-1 compound, which method comprises heating a solution of said GLP-1 compound having a pH between pH 8.0 to pH 10.0 to a temperature between 50° C. and 80° C. for a period of time which is between 3 minutes and 180 minutes.

In one embodiment the present invention relates to a method for preparation of a shelf-stable pharmaceutical composition of a GLP-1 compound, which method comprises heating a solution of said GLP-1 compound having a pH between pH 8.0 to pH 10.0 to a temperature between 50° C. and 80° C. for a period of time which is between 3 minutes and 120 minutes.

In another aspect the present invention relates to a method for the treatment of hyperglycemia comprising parenteral administration of an effective amount of the pharmaceutical composition according to the invention to a mammal in need of such treatment.

In another aspect the present invention relates to a method for the treatment of obesity, beta-cell deficiency, IGT or dyslipidemia comprising parenteral administration of an effective amount of the pharmaceutical composition according to the invention to a mammal in need of such treatment.

EXAMPLES

General Procedure

Thioflavin T (ThT) Fibrillation Assay: Principle and Examples

Low physical stability of a peptide may lead to amyloid fibril formation, which is observed as well-ordered, thread-like macromolecular structures in the sample eventually resulting in gel formation. This has traditionally been measured by visual inspection of the sample. However, that kind of measurement is very subjective and depending on the observer. Therefore, the application of a small molecule indicator probe is much more advantageous. Thioflavin T (ThT) is such a probe and has a distinct fluorescence signature when binding to fibrils [Naiki et al. (1989) Anal. Biochem. 177, 244-249; LeVine (1999) Methods. Enzymol. 309, 274-284].

Figure 6:
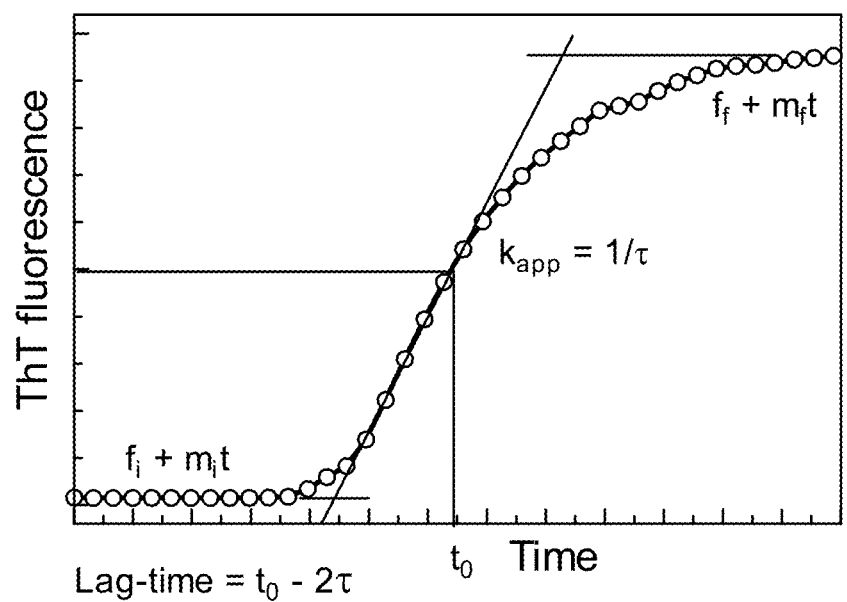
FIG. 6. Time course for fibril formation.

The time course for fibril formation can be described by a sigmoidal curve with the following expression [Nielsen et al. (2001) Biochemistry 40, 6036-6046], cn.f FIG. 6:

$$F = f_i + m_i t + \frac{f_f + m_f t}{1 + e^{-[(t-t_0)/\tau]}} \quad \text{Eq. (1)}$$

Here, F is the ThT fluorescence at the time t. The constant $t_0$ is the time needed to reach 50% of maximum fluorescence. The two important parameters describing fibril formation are the lag-time calculated by $t_0 - 2\tau$ and the apparent rate constant $k_{app} = 1/\tau$.

Formation of a partially folded intermediate of the peptide is suggested as a general initiating mechanism for fibrillation. Few of those intermediates nucleate to form a template onto which further intermediates may assembly and the fibrillation proceeds. The lag-time corresponds to the interval in which the critical mass of nucleus is built up and the apparent rate constant is the rate with which the fibril itself is formed.

Sample Preparation

Samples were prepared freshly before each assay. Each sample composition is described in the legends. The pH of the sample was adjusted to the desired value using appropriate amounts of concentrated NaOH and $HClO_4$. Thioflavin T was added to the samples from a stock solution in $H_2O$ to a final concentration of 1 µM.

Sample aliquots of 200 µl were placed in a 96 well microtiter plate (Packard OptiPlate™-96, white polystyrene). Usually, eight replica of each sample (corresponding to one test condition) were placed in one column of wells. The plate was sealed with Scotch Pad (Qiagen).

Incubation and Fluorescence Measurement

Incubation at given temperature, shaking and measurement of the ThT fluorescence emission were done in a Fluoroskan Ascent FL fluorescence platereader (Thermo Labsystems). The temperature was adjusted to 37° C. The orbital shaking was adjusted to 960 rpm with an amplitude of 1 mm in all the presented data. Fluorescence measurement was done using excitation through a 444 nm filter and measurement of emission through a 485 nm filter.

Each run was initiated by incubating the plate at the assay temperature for 10 min. The plate was measured every 20 minutes for typically 45 hours. Between each measurement, the plate was shaken and heated as described.

Data Handling

The measurement points were saved in Microsoft Excel format for further processing and curve drawing and fitting was performed using GraphPad Prism. The background emission from ThT in the absence of fibrils was negligible. The data points are typically a mean of eight samples and shown with standard deviation error bars. Only data obtained in the same experiment (i.e. samples on the same plate) are presented in the same graph ensuring a relative measure of fibrillation between the individual samples of one assay rather than comparison between different assays.

The data set may be fitted to Eq. (1). However, since full sigmodial curves in this case are not usually achieved during the measurement time, the degree of fibrillation is expressed as ThT fluorescence at various time points calculated as the mean of the eight samples and shown with the standard deviation.

Example 1

The ThT fibrillation assay of a pharmaceutical composition of the acylated GLP-1 analogue liraglutide is shown in FIG. 1 (experimental performed along procedures described in "General procedure"). After approximately 10 hours the ThT fluorescence emission increases indicating the on-set of fibrillation. This signal increases steadily and reaches a plateau before the assay is terminated. In the presence of 200 ppm Poloxamer 188, however, the ThT fluorescence signal remains at the background level. This indicates that no fibrillation occurs and, hence, the pharmaceutical composition is physical stable under these conditions. The pharmaceutical compositions used in example 1 (FIG. 1) is not added a buffer.

Example 2

Figure 2:
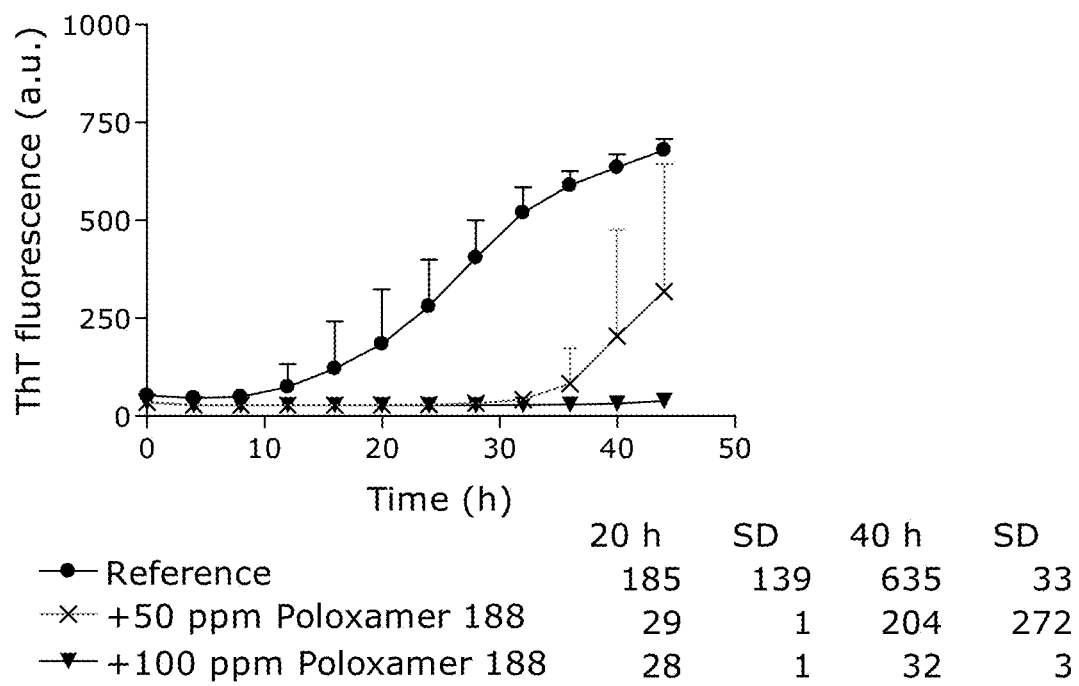
FIG. 2. All samples contain 1.67 mM Liraglutide, 58 mM phenol, 14 mg/ml propylene glycol, 8 mM sodium phosphate pH 7.7. Poloxamer 188 is added to two samples.

The effect of Poloxamer 188 in a pharmaceutical composition of liraglutide containing sodium phosphate as a buffer is shown in FIG. 2 (experimental performed along procedures described in "General procedure"). Here, the presence of 50 ppm Poloxamer 188 prolongs the lag time before on-set of fibrillation, whereas 100 ppm Poloxamer 188 completely inhibits fibrillation during the assay time.

Example 3

Figure 3:
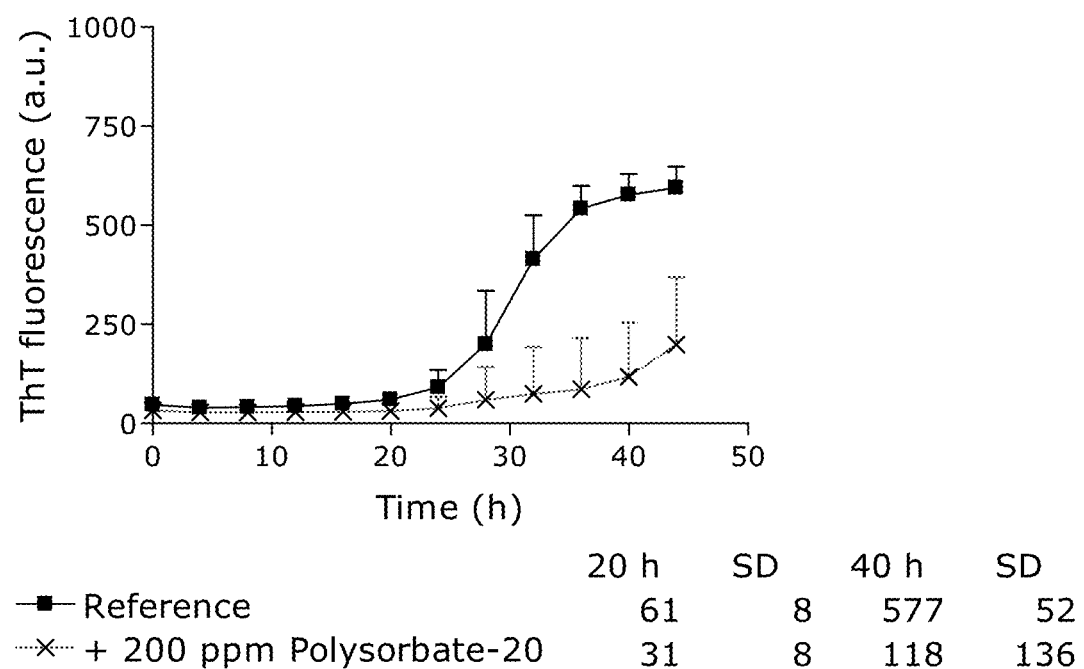
FIG. 3. Both samples contain 1.2 mM Liraglutide, 40 mM phenol, 14 mg/ml propylene glycol, 10 mM NaCl, pH 7.7. Polysorbate 20 added to one sample FIG. 4. Measurement of NTU versus time during a rotation test of liraglutide compositions without surfactant (F1) and with surfactant (F2 and F3).

Polysorbate 20 does also stabilise formulations of liraglutide. One such example is shown in FIG. 3 (experimental performed along procedures described in "General procedure"). The presence of 200 ppm Polysorbate 20 attenuates the fibrillation, which is observed as a slower growth rate of the ThT fluorescence signal. Hence, a significantly smaller ThT fluorescence signal is observed in the Polysorbate 20 sample than in the reference after 40 hours of incubation.

Example 4

Two pharmaceutical compositions are prepared :
F1. 1.2 mM liraglutide, 14 mg/ml propylene glycol, 40 mM phenol, 3 Zn/hexamer, aspart 0.6 mM, 8 mM bicine, 50 ppm poloxamer 188, pH 7.7.
F2. 1.2 mM liraglutide, 14 mg/ml propylene glycol, 40 mM phenol, 3 Zn/hexamer, aspart 0.6 mM, 8 mM bicine, pH 7.7.

Physical stability of the pharmaceutical compositions are evaluated by means of an accelerated stressed test. The stressed test is performed as a rotation test. 50 µL air is added to 5 cartridges (glass vials) of each formulation. The cartridges are rotated with a frequency of 30 rotations per minute for 4 hours daily. The test is stopped after 22 days of rotation. The inspection of the cartridges is followed daily or as required. The turbidity of the pharmaceutical compositions is characterized by nephelometric measurement of the turbidity on a HACH Turbidimeter 2100AN. The turbidity measurement of a liquid is specified in "Nephelometric Turbidity Unit" (NTU). Physical instability of the protein is characterised by high turbidity measurements.

The experiment shows that composition F2 has a much more rapid increase in NTU as compared to that of the F1 composition.

Example 5

Three pharmaceutical compositions were prepared:
F1. 1.6 mM liraglutide, 14 mg/ml propylene glycol, 40 mM phenol, 8 mM sodium phosphate, pH 7.7.
F2. 1.6 mM liraglutide, 14 mg/ml propylene glycol, 40 mM phenol, 8 mM sodium phosphate, 100 µg/ml poloxamer 188, pH 7.7.
F3. 1.6 mM liraglutide, 14 mg/ml propylene glycol, 40 mM phenol, 8 mM sodium phosphate, 200 µg/ml poloxamer 188, pH 7.7.

Figure 4:
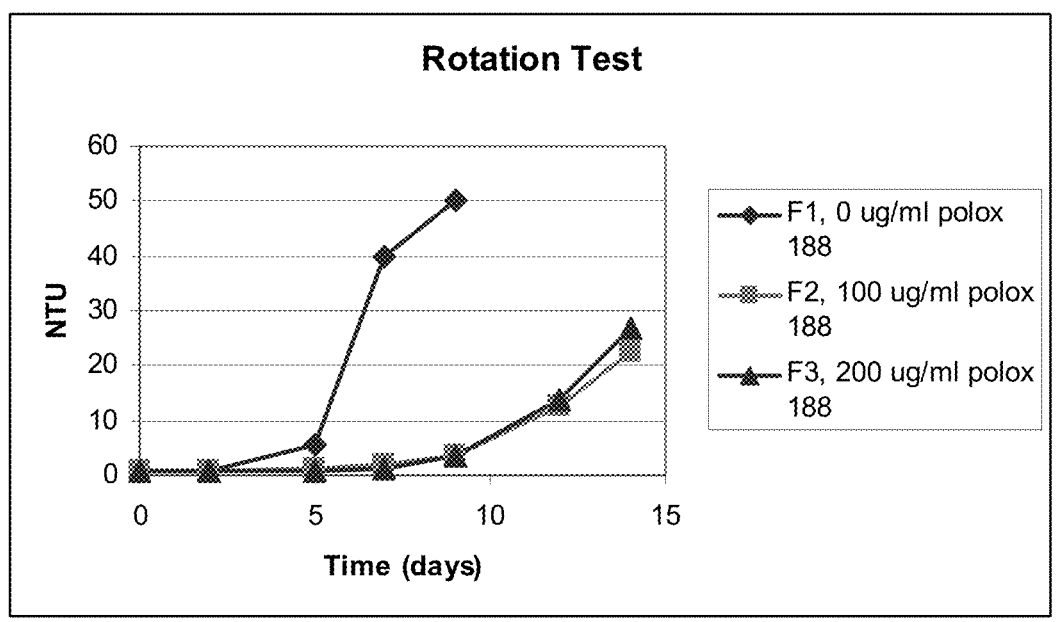

The pharmaceutical compositions F1-F3 were subjected to the rotation test as described in example 4. The resulting NTU measurements versus time are shown in FIG. 4.

Example 6

Two pharmaceutical compositions were prepared:
F1. 1.6 mM liraglutide, 14 mg/ml propylene glycol, 40 mM phenol, 8 mM sodium phosphate, 0 µg/ml poloxamer 407 (Pluronic F-127), pH 7.7.
F2. 1.6 mM liraglutide, 14 mg/ml propylene glycol, 40 mM phenol, 8 mM sodium phosphate, 200 µg/ml poloxamer 407 (Pluronic F-127), pH 7.7.

Figure 5:
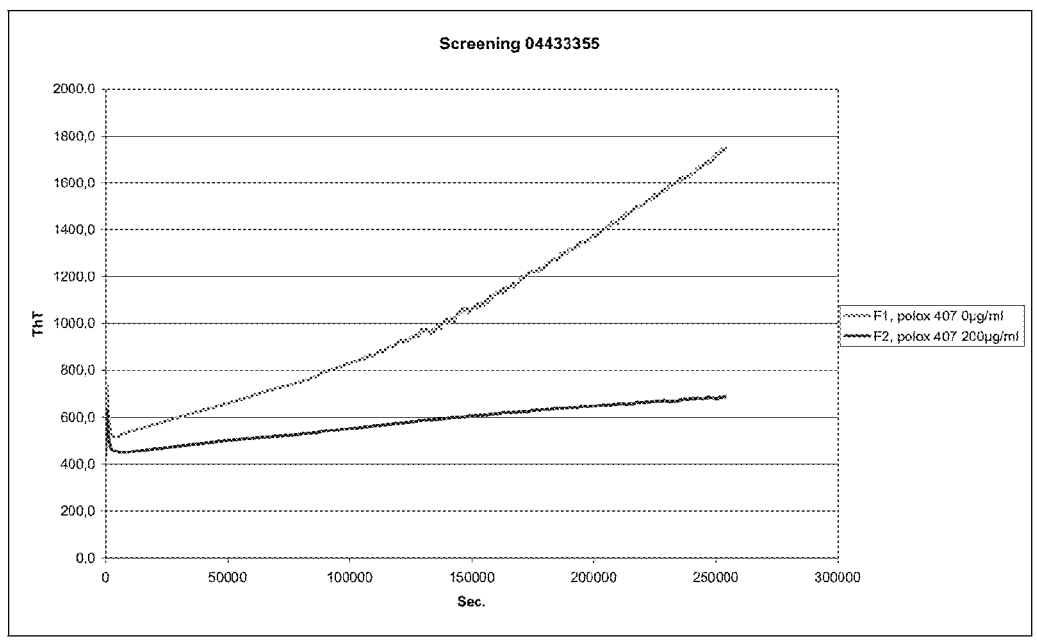
FIG. 5. Measurement of ThT fluorescence versus time during a rotation test of liraglutide compositions without surfactant (F1) and with surfactant (F2). The lower curve is the trace of F2.

The formulations were tested with respect to physical stability using the Thioflavin T assay. The formulations are placed in 96-well plates (Black NUNC) and incubated at 37° C. for up to 72h at the BMG FLUOstar microtiterplate fluorimeter using the following program: [300 rpm 15 min, 5 min rest]$_{n=72}$. The resulting measurements are shown in FIG. 5 (lower curve being F2)

Example 7

Solution 1 was prepared by dissolving preservative, isotonic agent, and buffer in water, pH was adjusted to 7.3. In another container solution 2 was prepared: liraglutide was dissolved in 60° C. hot water and kept on a water bath at 60° C. for 1, 20, and 120 minutes. The heat treatment of liraglutide was carried out in solution having pHs of about 8 and 10. After heat treatment solution 2 was cooled to 22° C. where after the two solutions were mixed and pH adjusted to 7.7 using sodium hydroxide and/or hydrochloric acid. Finally, the formulation was filtered through a 0.22 µm filter.

The physical stability of the liraglutide preparations was evaluated by the use of a florescence method; the Thioflavine T-test where the histological thiazole dye Thioflavine T (ThT) was used as an indicator of fibril formation. By the use of Thioflavine T-test it was possible to determine the presence of fibrils in the different formulations. The method was based on the fluorescent characteristics of ThT. In the presence of fibrils, the fluorescence of ThT exhibited an excitation maximum at 450 nm and enhanced emission at 482 nm. The ThT fluorescence intensity has been shown to be linear with an increase in fibril concentration.

ThT was used in a stress test applying the different formulations in microtiter plates with ThT at 35° C. and shaken with 350 rpm until the formulations were fibrillated. Graphs of the fluorescence intensity (FI) as a function of time (sec) were obtained. The response variable was; time (seconds) to achieve a fluorescence intensity of 400, e.g. the longer time to reach FI=400, the more stable a formulation.

The purity of the liraglutide preparations was measured by RP-HPLC.

Figure 7:
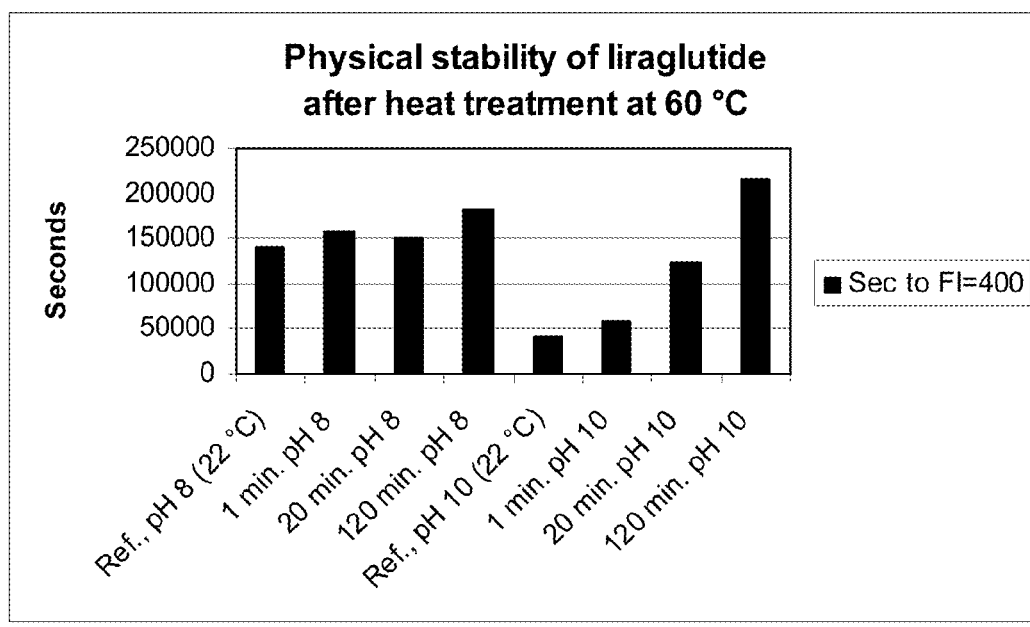
FIG. 7. Physical stability of liraglutide prepared by heat treatment at 60° C.
Figure 8:
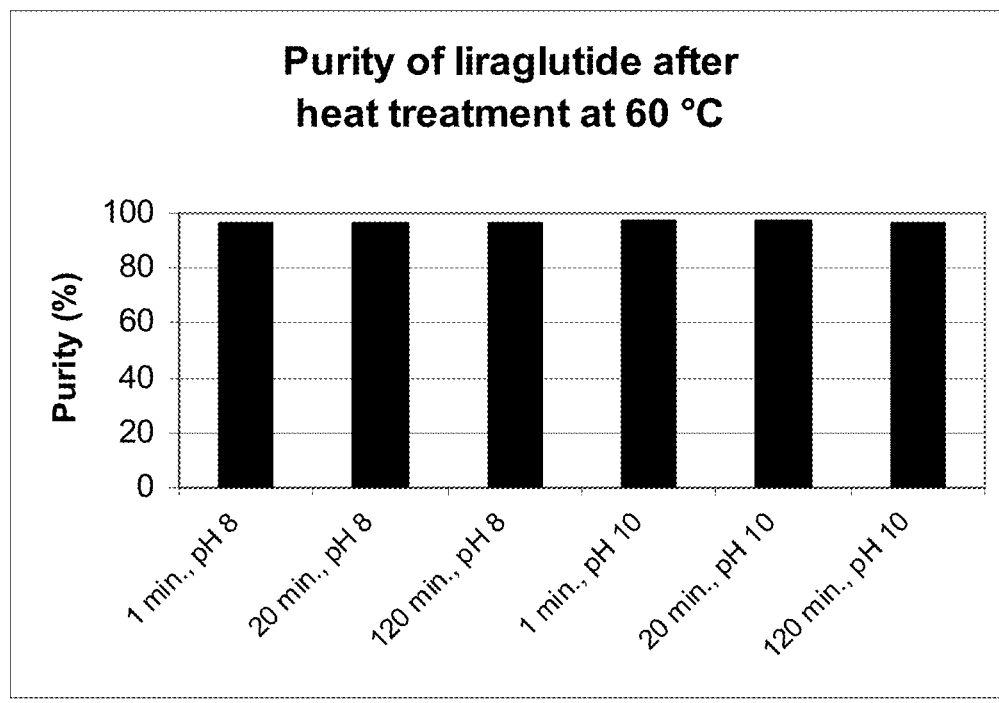
FIG. 8. Purity of liraglutide after heat treatment at 60° C.

Results from the experiments are depicted in FIGS. 7 and 8.

Example 8

Solution 1 was prepared by dissolving preservative, isotonic agent, and buffer in water, pH was adjusted to 7.3. In another container solution 2 was prepared: liraglutide was dissolved in 80° C. hot water and kept on a water bath at 80° C. for 1, 30, and 120 minutes. The heat treatment of liraglutide was carried out in solution having pHs of about 8 and 10. After heat treatment solution 2 was cooled to 22° C. where after the two solutions were mixed and pH adjusted to 7.7 using sodium hydroxide and/or hydrochloric acid. Finally, the formulation was filtered through a 0.22 µm filter.

Figure 9:
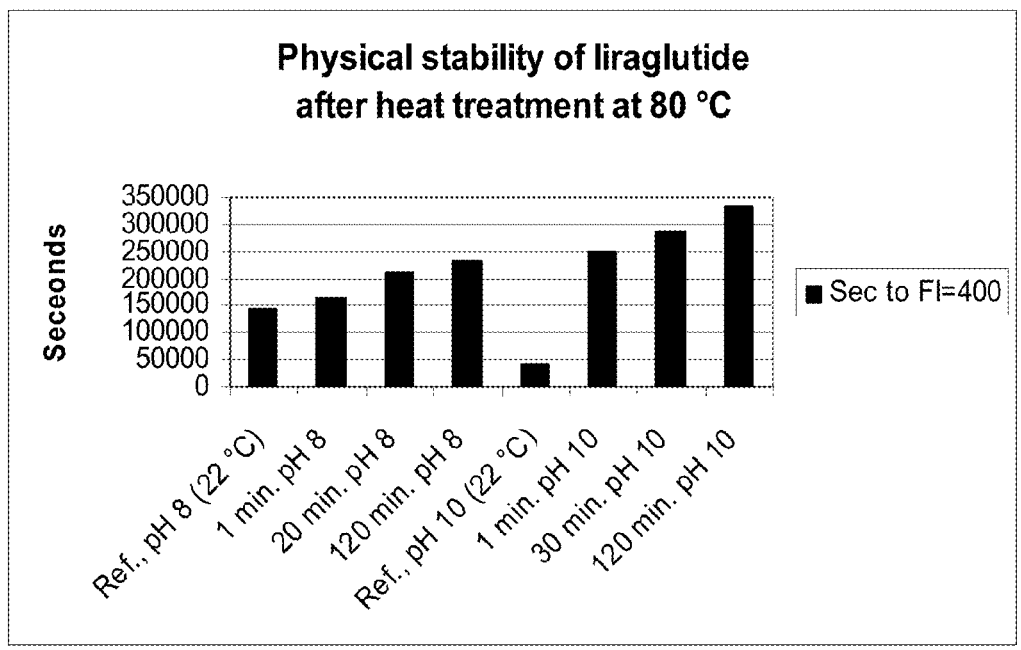
FIG. 9. Physical stability of liraglutide prepared by heat treatment at 80° C.
Figure 10:
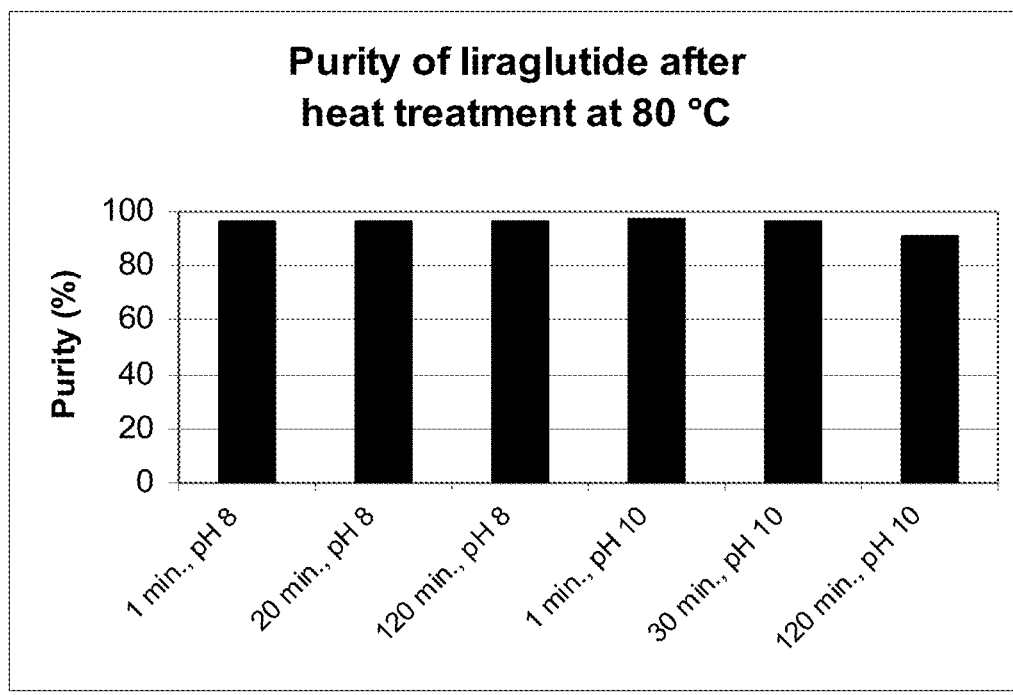
FIG. 10. Purity of liraglutide after heat treatment at 80° C.

Physical stability and purity of the preparations were measured as described in example 7. Results from the experiments are depicted in FIGS. 9 and 10.

Example 9

Solution 1 was prepared by dissolving preservative, isotonic agent, and buffer in water, pH was adjusted to 7.3. In another container solution 2 was prepared: liraglutide was dissolved in water of various temperatures: 22, 40, 60, and 80° C. and kept on a water bath for 15 minutes for all the investigated temperatures. The heat treatments of liraglutide were carried out in solution having a pH of about 10. After heat treatment solution 2 was cooled to 22° C. where after the two solutions were mixed and pH adjusted to 7.7 using sodium hydroxide and/or hydrochloric acid. Finally, the formulation was filtered through a 0.22 µm filter.

Physical stability of the preparations was measured as described in example 7.

Figure 11:
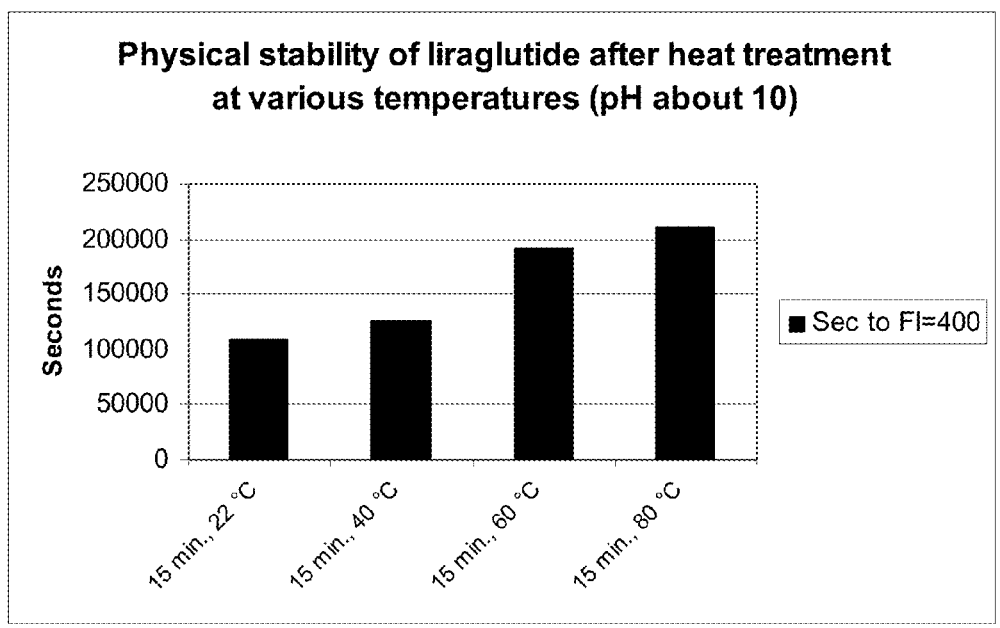
FIG. 11. Physical stability of liraglutide prepared by 15 min. of heat treatment at 22, 40, 60, and 80° C.

Results from the experiments are depicted in FIG. 11.

Example 10

Heat treatment during preparation (30, 60, and 120 min. at 60° C. compared to 60 min. at 22° C.) followed by formulation of drug product at pH of 8.15 is performed. Furthermore, the investigation of an additive effect of heat treatment (1 and 3 min. at 80° C.) of liraglutide drug substance prior to freeze drying followed by a second heat treatment (8 min. at 75° C.) of liraglutide during preparation is performed.

Example 11 liraglutide was dissolved in water at room temperature and pH was adjusted to pH 10. The solution was heated on a water bath at 50 and 80° C. for 1, 3, 5 and 20 minutes. After heat treatment, the solution was cooled to 22° C. on a water batch. The solution was then filtered through a 0.22 µm filter and freeze dried. The powder was dissolved in a solution containing preservative, isotonic agent and buffer components and pH was adjusted to pH 7.7.

The physical stability of heat treated liraglutide preparations was evaluated by the use of the Thioflavin T method described in example 7. Chemical stability of the preparations were measured using reversed phase HPLC.

Figure 12:
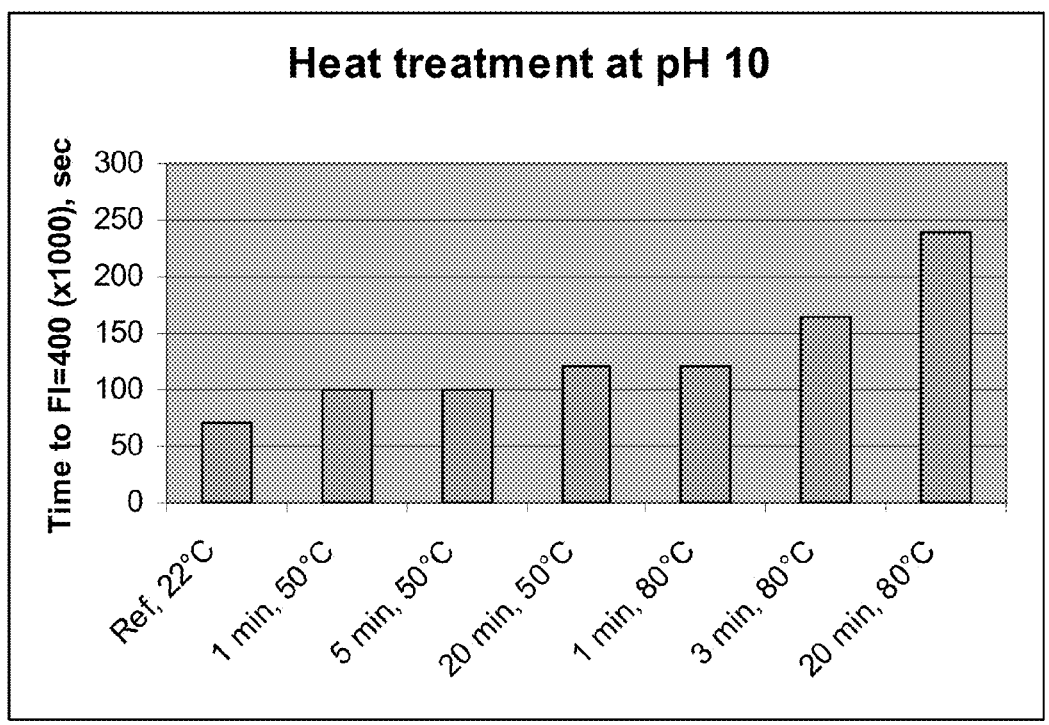
FIG. 12. Physical stability of liraglutide prepared by heat treatment at 50 and 80° C. at pH 10.
Figure 13:
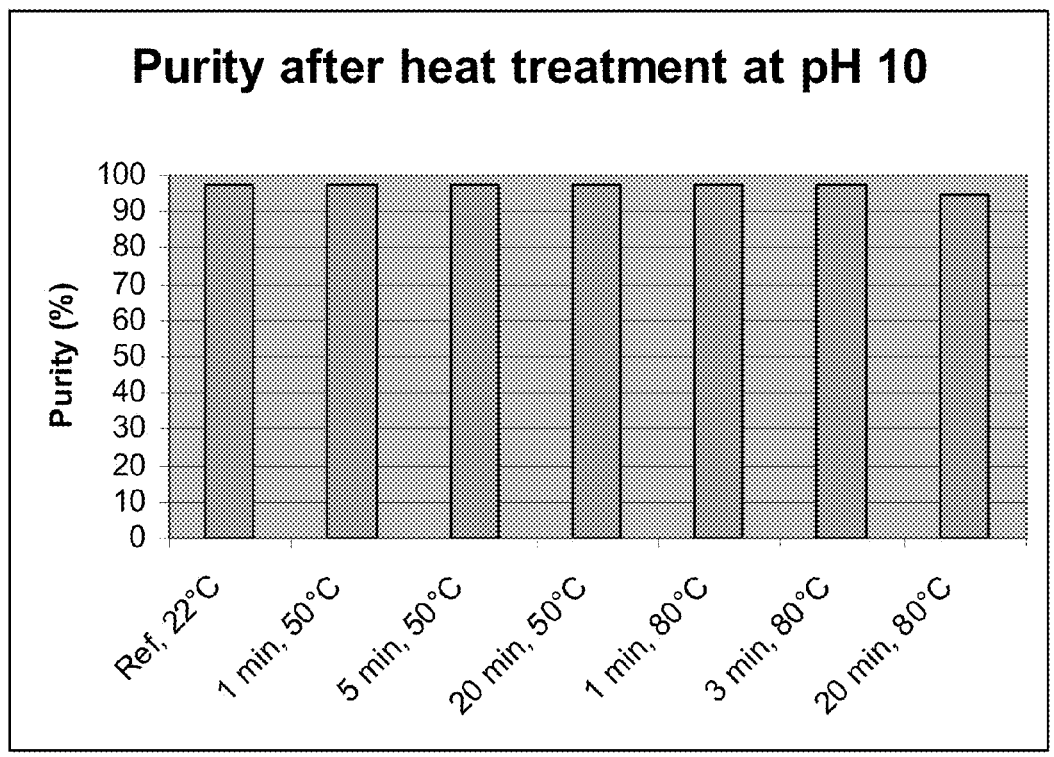
FIG. 13. Purity of liraglutide after heat treatment at 50 and 80° C. at pH 10.

The results are depicted in FIGS. 12 and 13.

Example 12 liraglutide was dissolved in water at room temperature and pH was adjusted to pH 9 and 10. The solution was heated on a water bath at 60 and 80° C. for 1 and 15 minutes. After heat treatment, the solution was cooled to 22° C. on a water batch. The solution was then filtered through a 0.22 µm filter and freeze dried. The powder was dissolved in a solution containing preservative, isotonic agent and buffer components and pH was adjusted to pH 7.7.

The physical stability of heat treated liraglutide preparations was evaluated by the use of the Thioflavin T method described in example 7. Chemical stability of the preparations were measured using reversed phase HPLC.

Figure 14:
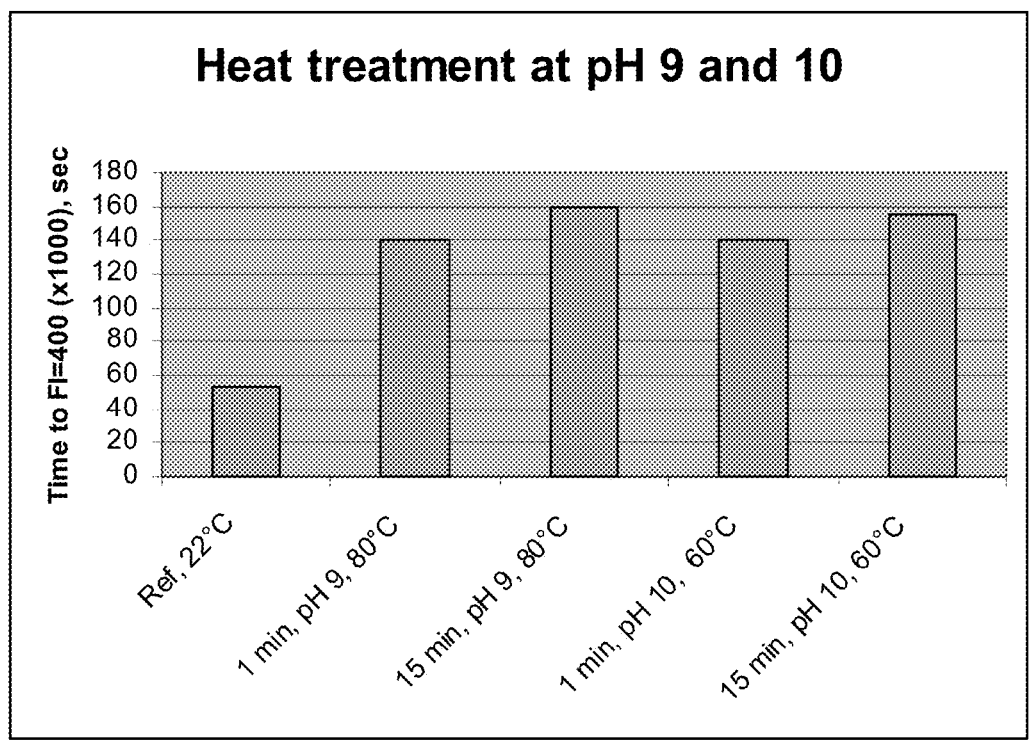
FIG. 14. Physical stability of liraglutide prepared by heat treatment at 60 and 80° C. at pH 9 and 10.
Figure 15:
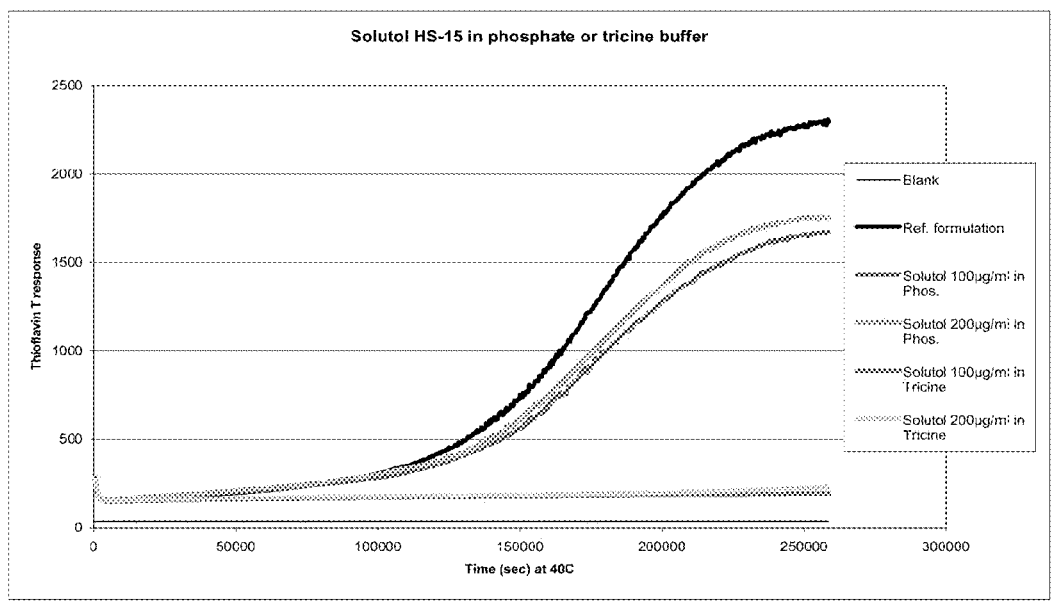
FIG. 15. This figure shows 5 different formulations. 4 different formulations containing various amounts of Solutol HS-15 in either phosphate or tricine buffer. One formulation (Ref. formulation) is liraglutide in phosphate buffer without surfactant.
Figure 16:
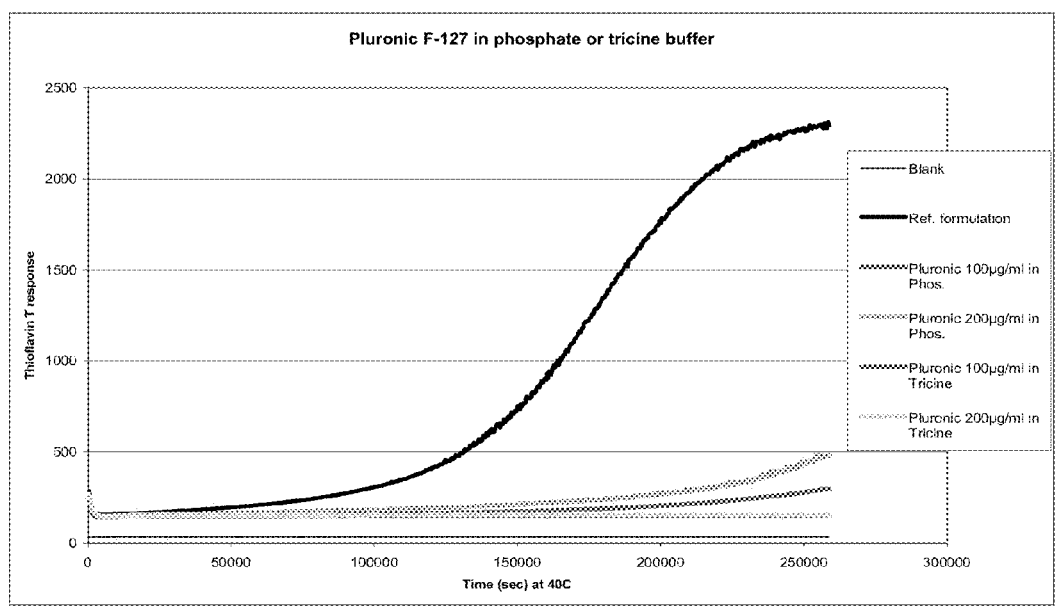
FIG. 16. This figure shows 5 different formulations. 4 different formulations containing various amounts of Pluronic F-127 in either phosphate or tricine buffer. One formulation (Ref. formulation) is liraglutide in phosphate buffer without surfactant.

The results are depicted in FIG. 14.

Example 13

The formulations were mixed according to tables 1 and 2.

TABLE 1

Excipients held constant

| Parameter | Concentration |
| --- | --- |
| Liraglutide | 6.25 mg/ml |
| Propylene glycol | 14.0 mg/ml |
| Phenol | 5.50 mg/ml |
| Thioflavin T | 1 mM | pH = 7.7

TABLE 2

Specific excipients.

| Excipients | Concentration |
| --- | --- |
| Solutol HS-15 | 100 or 200 µg/ml |
| Pluronic F-127 (Poloxamer 407) | 100 or 200 µg/ml |
| Di-sodium hydrogen phosphate, di-hydrate | 8 mM |
| Tricine | 10 mM |

8×250 µl of each formulation (8 repeats) was pipetted into a 96-well plate (Black NUNC). Subsequently, the plates were sealed using "Sealing tape for plates, NUNC".

The plate was inserted into a BMG FLUOstar microtiter plate fluorimeter. Excitation was measured at 440±10 mm and emission at 480±10 mm. Data were sampled for 72 h (approx. 260.000 sec). The BMG FLUOstar microtiter plate fluorimeter was programmed as indicated here: [600 rpm for 300 sec, rest 100 sec]$_{n=72}$ using double orbital rotation.

From what can be seen in FIGS. 1 and 2, the formulations containing Solutol HS-15 in phosphate buffer are only slightly more stable than the reference formulation. The formulations containing either 100 or 200 µg/ml Pluronic F-127 in phosphate buffer are more stable. Interestingly, formulations containing either Solutol HS-15 or Pluronic F-127 in tricine buffer are exceptionally stable, especially the latter.

Example 14

Solution 1 was prepared by dissolving preservative, isotonic agent, and buffer in water, pH was adjusted to 7.9. In another container solution 2 was prepared: liraglutide was dissolved in 60-70° C. hot water and kept on a water bath at 50, 60, and 70° C. for 60, 90, and 20 minutes. The heat treatment of liraglutide was carried out in solution having pHs of about 8 and 10. After heat treatment solution 2 was cooled to 22° C. where after the two solutions were mixed and pH adjusted to 8.15 using sodium hydroxide and/or hydrochloric acid. Finally, the formulation was filtered through a 0.22 µm filter.

The physical stability of the liraglutide preparations were evaluated by the use of a florescence method; the Thioflavine T-test where the histological thiazole dye Thioflavine T (ThT) was used as an indicator of fibril formation. By the use of Thioflavine T-test it was possible to determine the presence of fibrils in the different formulations. The method was based on the fluorescent characteristics of ThT. In the presence of fibrils, the fluorescence of ThT exhibited an excitation maximum at 450 nm and enhanced emission at 482 nm. The ThT fluorescence intensity has been shown to be linear with an increase in fibril concentration.

ThT was used in a stress test applying the different formulations in microtiter plates with ThT at 35° C. and shaken with 350 rpm until the formulations were fibrillated. Graphs of the fluorescence intensity (FI) as a function of time (sec) were obtained. The response variable was; time (sec) to achieve a fluorescence intensity of 400, e.g. the longer time to reach FI=400, the more stable a formulation.

Figure 17:
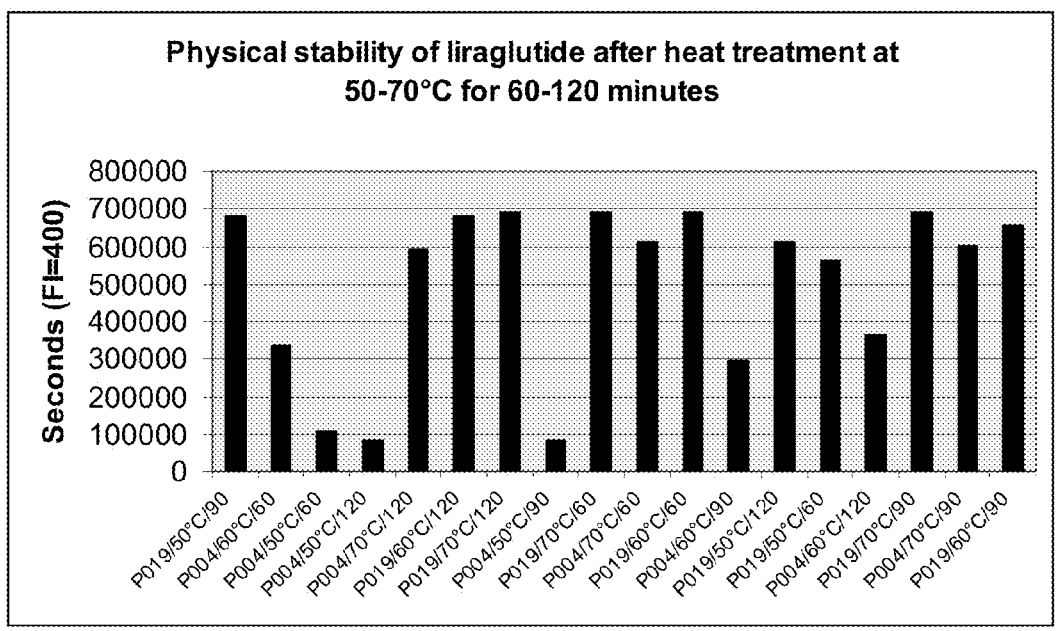
FIG. 17. Physical stability of liraglutide after heat treatment at 50-70° C. for 60-120 minutes.

The results are depicted in FIG. 17.

Example 15

Solution 1 was prepared by dissolving preservative, isotonic agent, and buffer in water, pH was adjusted to 7.9. In another container solution 2 was prepared: liraglutide was dissolved in 60-70° C. hot water and kept on a water bath at 60, 65, and 70° C. for 30, 45, 150, and 180 minutes. The heat treatment of liraglutide was carried out in solution having pHs of about 8 and 10. After heat treatment solution 2 was cooled to 22° C. where after the two solutions were mixed and pH adjusted to 8.15 using sodium hydroxide and/or hydrochloric acid. Finally, the formulation was filtered through a 0.22 µm filter.

The physical stability of the liraglutide preparations were evaluated by the use of a florescence method as described in example 14.

Example 16

Heat treatment of liraglutide drug product in Penfill®.

TABLE 1

| Penfill ® containing fibrillated liraglutide were heat treated for 30 min at 85° C. ||
| --- | --- |
| Penfill before heat treatment (NTU) | Penfill after heat treatment (NTU) |
| Approx. 50 (average of 10 penfill containing fibrillated liraglutide DP) | 0.382 |
|  | 0.182 |
|  | 0.275 |
|  | 0.174 |
|  | 0.284 |
|  | 0.356 |
|  | 0.24 |
|  | 0.326 |
|  | 0.19 |
|  | 0.836 |

Freshly produced liraglutide drug product has a turbidity of approx. 0.2-1.0 NTU. Thus, heat treatment of highly fibrillated liraglutide drug product can dissolve the otherwise very stable fibril structures.

Figure 18:
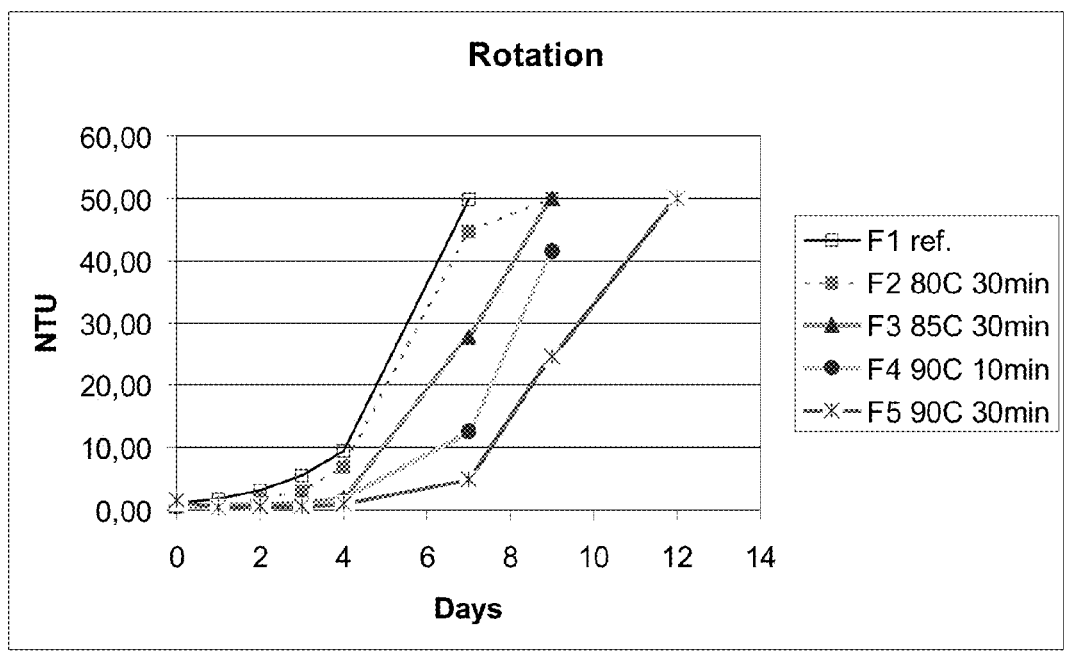
FIG. 18. Penfill® heat treated at different times and temperatures which were subsequently subjected to rotation.
Figure 19:
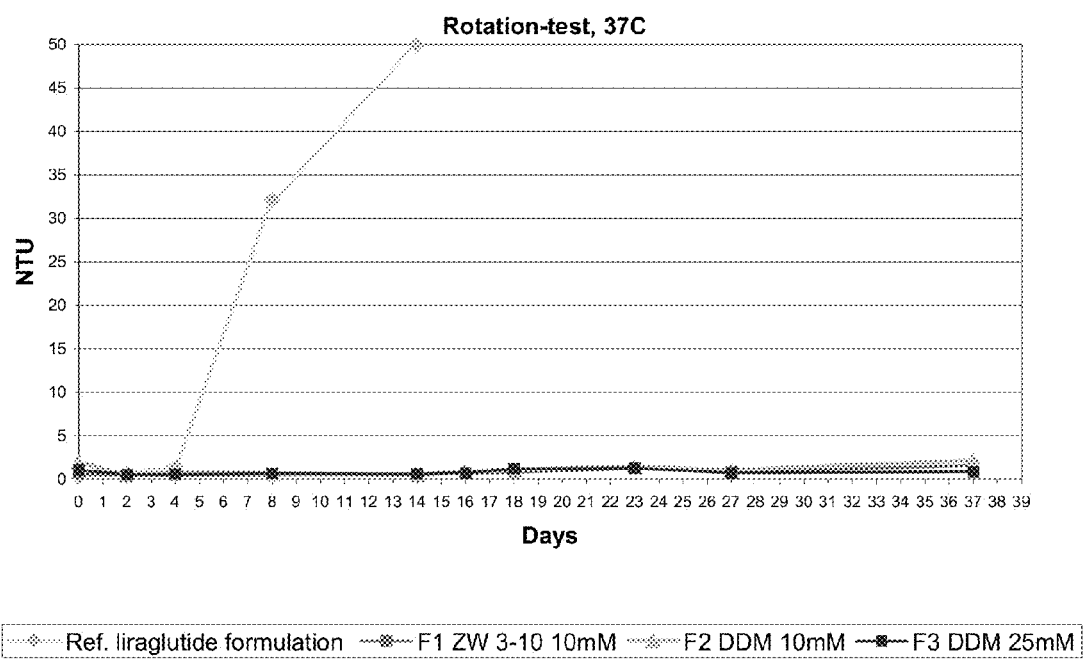
Figure 20:
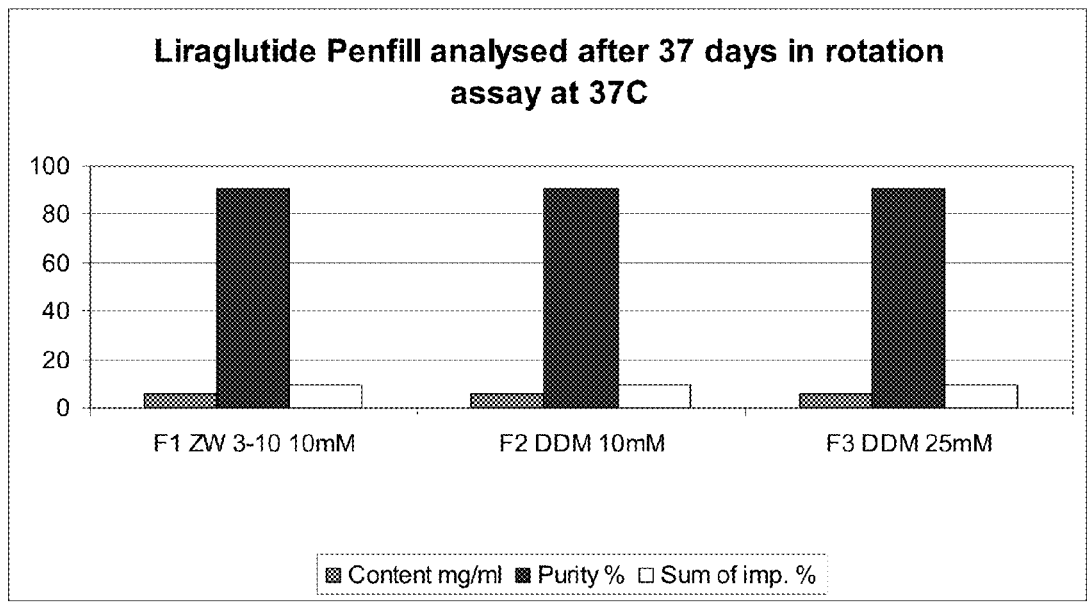

FIG. 18 shows Penfill® heat treated at different times and temperatures which were subsequently subjected to rotation.

The invention claimed is:

1. A method for the preparation of a shelf-stable pharmaceutical composition of a GLP-1 compound comprising: dissolving said GLP-1 compound in aqueous medium, adjusting the pH of the solution to between about 8.0 and about 10.5, and heating the solution to a temperature between about 50° C. and about 95° C. for a period of time from about 3 minutes to about 180 minutes to result in a shelf-stable pharmaceutical solution.

2. The method according to claim 1, wherein the temperature is between 60° C. and 95° C.

3. The method according to claim 1, wherein the temperature is between 50° C. and 80° C.

4. The method according to claim 1, wherein the temperature is between 70° C. and 80° C.

5. The method according to claim 1, wherein the temperature is between 60° C. and 80° C.

6. The method according to claim 1, wherein the pH is between about 8.0 to 10.0.

7. The method according to claim 1, wherein the pH is about 8.15.

8. The method according to claim 1 wherein the heating is continued for a period of time which is between 15 minutes and 120 minutes.

9. The method according to claim 1 wherein the heating is continued for a period of time which is between 10 minutes and 90 minutes.

10. The method according to claim 1 wherein the heating is continued for a period of time which is between 3 minutes and 30 minutes.

11. The method according to claim 1 wherein the heating is continued for a period of time which is between 5 minutes and 15 minutes.

12. The method according to claim 1, further comprising freeze drying the solution after the heating step; wherein the resulting freeze-dried composition is shelf-stable.

13. The method according to claim 1, further comprising the addition of a pharmaceutically acceptable excipient after the heating step; wherein the resulting pharmaceutical composition is shelf-stable.

14. The method according to claim 1, wherein said GLP-1 compound is $Arg^{34}$, $Lys^{26}(N^{\epsilon}\text{-}(\gamma\text{-}Glu(N^{\alpha}\text{-hexadecanoyl})))\text{-}GLP\text{-}1(7\text{-}37)$.

* * * * *

UNITED STATES PATENT AND TRADEMARK OFFICE
CERTIFICATE OF CORRECTION

| | | |
|---|---|---|
| PATENT NO. | : 8,748,376 B2 | Page 1 of 1 |
| APPLICATION NO. | : 12/643330 | |
| DATED | : June 10, 2014 | |
| INVENTOR(S) | : Ludvigsen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 683 days.

Signed and Sealed this
Twenty-fifth Day of August, 2015

Michelle K. Lee
*Director of the United States Patent and Trademark Office*